(12) United States Patent
Scheinberg et al.

(10) Patent No.: US 9,045,756 B2
(45) Date of Patent: Jun. 2, 2015

(54) COMPOSITIONS AND METHODS FOR TREATING CANCER AND OTHER DISEASES

(75) Inventors: David A. Scheinberg, New York, NY (US); Prabodhika Mallikaratchy, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 73 days.

(21) Appl. No.: 13/510,221

(22) PCT Filed: Nov. 16, 2010

(86) PCT No.: PCT/US2010/056881
§ 371 (c)(1),
(2), (4) Date: May 16, 2012

(87) PCT Pub. No.: WO2011/060435
PCT Pub. Date: May 19, 2011

(65) Prior Publication Data
US 2012/0225088 A1    Sep. 6, 2012

Related U.S. Application Data

(60) Provisional application No. 61/261,731, filed on Nov. 16, 2009, provisional application No. 61/394,736, filed on Oct. 19, 2010.

(51) Int. Cl.
| | |
|---|---|
| *C07H 21/02* | (2006.01) |
| *C07H 21/04* | (2006.01) |
| *C12N 15/115* | (2010.01) |
| *A61K 31/711* | (2006.01) |
| *C12Q 1/68* | (2006.01) |

(52) U.S. Cl.
CPC ............ *C12N 15/115* (2013.01); *A61K 31/711* (2013.01); *C12N 2310/16* (2013.01)

(58) Field of Classification Search
None
See application file for complete search history.

(56) References Cited

U.S. PATENT DOCUMENTS

| | | | |
|---|---|---|---|
| 8,637,656 B2 * | 1/2014 | Nakamura et al. | 536/24.5 |
| 2006/0105975 A1 * | 5/2006 | Pendergrast et al. | 514/44 |
| 2006/0264369 A1 | 11/2006 | Diener et al. | |
| 2007/0009476 A1 | 1/2007 | Wilson et al. | |
| 2008/0026947 A1 | 1/2008 | Gmeiner | |
| 2009/0081679 A1 | 3/2009 | Keefe et al. | |
| 2009/0130650 A1 | 5/2009 | Tan et al. | |

FOREIGN PATENT DOCUMENTS

CN          101537189          9/2009

OTHER PUBLICATIONS

Zhou et al. Chemistry and Biology vol. 15:644-645, Jul. 21, 2008.*
International Search Report of Application No. PCT/US10/56881 Date of Mailing Apr. 7, 2011.
Zhao et al. GenBank Accession No. BH076467. RPCI-24-377G20. TJ RPCI-24 Mus musculus genomic clone RPCI-24-377G20, genomic survey sequence. Jul. 18, 2001. Retrieved from the Internet Mar. 27, 2011: <http://www.ncbl.nlm.nih.gov/nucgss/BH076467>.
Mallikaratchy et al. Aptamer directly evolved from live cells recognizes membrane bound immunoglobin heavy mu chain in Burkitt's lymphoma cells. Mol. Cell. Proteomics 2007, 6(12):2230-238.
Mallikaratchy et al. A multivalent DNA aptamer specific for the B-cell receptor on human lymphoma and leukemia. Nucleic Acids Res. Oct. 10, 2010, 39(6):2458-246.

* cited by examiner

*Primary Examiner* — Sean McGarry
(74) *Attorney, Agent, or Firm* — Mark S. Cohen; Pearl Cohen Zedek Latzer Baratz LLP

(57) ABSTRACT

Aptamers and improved aptamers are provided with enhanced efficacy for binding to target molecules in vivo or for treating cancer or other diseases. Such improvements in aptamers are provided that enhance in vivo efficacy such as binding to the target molecule or enhancing anti-cancer activity. Such improvements also include stability to serum nucleases, reduced binding to a soluble form of the target molecule, increased avidity, affinity or specificity to the target molecule on a cell surface, increased lifetime in circulation, or any combination of the foregoing. Improvements are provided by truncation, multimerization, including at least one non-natural nucleic acid, adding a 3' or 5' polyethylene glycol, or any combination thereof. Aptamers for treatment of autoimmune diseases are also provided.

17 Claims, 14 Drawing Sheets

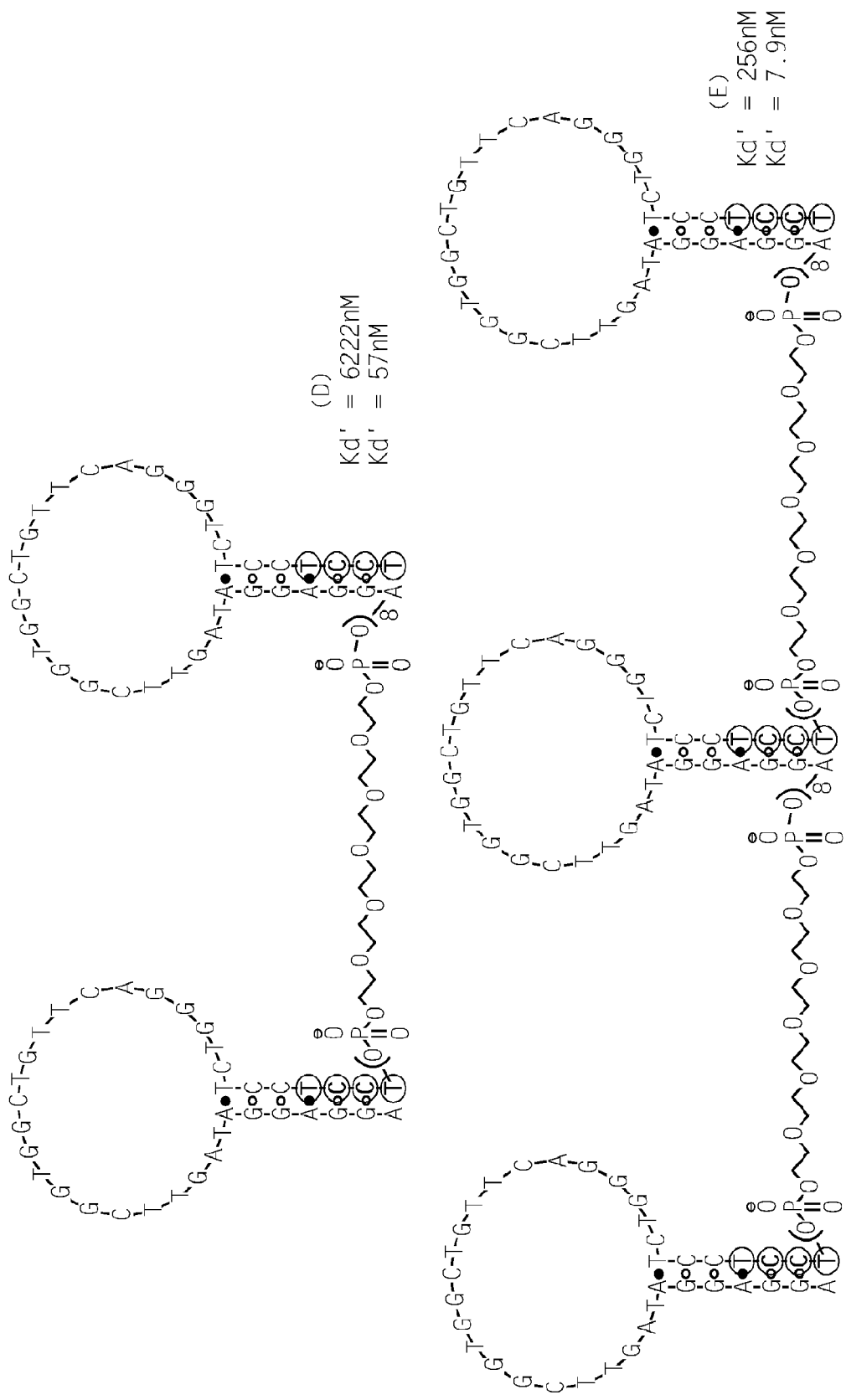

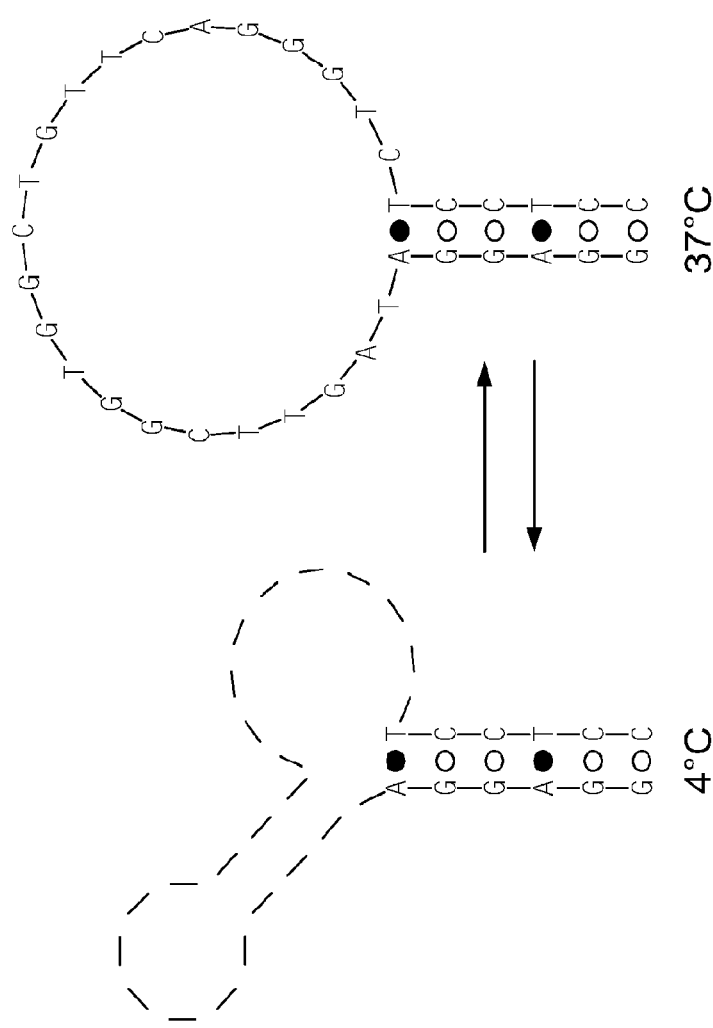
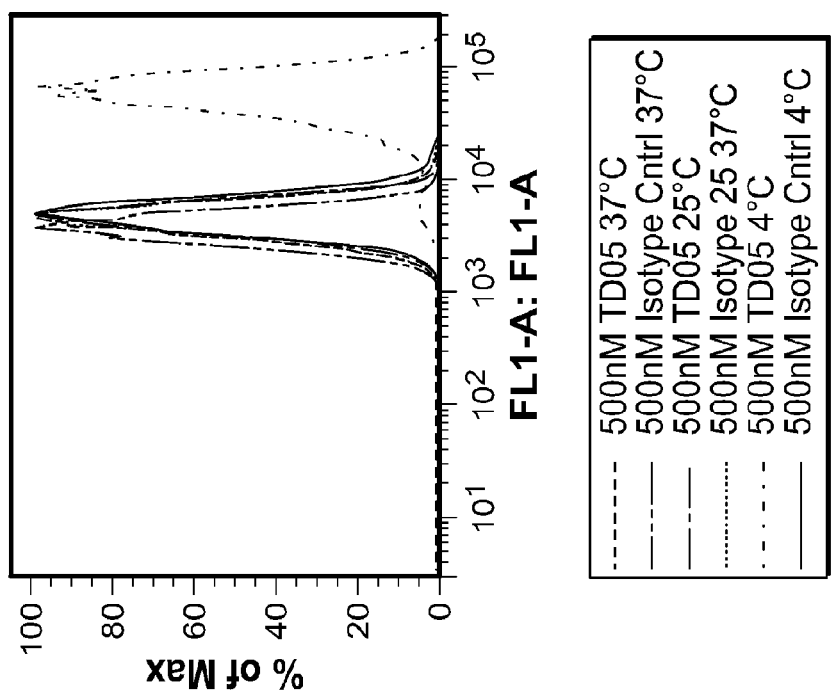
FIG. 7B
FIG. 7A

SEQUENCE LISTING

```
<160> NUMBER OF SEQ ID NOS: 24

<210> SEQ ID NO 1
<211> LENGTH: 45
<212> TYPE: DNA
<213> ORGANISM: Artificial Sequence
<220> FEATURE:
<223> OTHER INFORMATION: Synthetic aptamer

<400> SEQUENCE: 1
accgtggagg atagttcggt ggctgttcag ggtctcctcc acggt            45

<210> SEQ ID NO 2
<211> LENGTH: 38
<212> TYPE: DNA
<213> ORGANISM: Artificial Sequence
<220> FEATURE:
<223> OTHER INFORMATION: Synthetic aptamer

<400> SEQUENCE: 2
cgtggaggat agttcggtgg cttcagggtc tcctcccg                    38

<210> SEQ ID NO 3
<211> LENGTH: 37
<212> TYPE: DNA
<213> ORGANISM: Artificial Sequence
<220> FEATURE:
<223> OTHER INFORMATION: Synthetic aptamer

<400> SEQUENCE: 3
aggaggatag ttcggtggct gttcagggtc tcctcct                     37

<210> SEQ ID NO 4
<211> LENGTH: 35
<212> TYPE: DNA
```

```
<213> ORGANISM: Artificial Sequence
<220> FEATURE:
<223> OTHER INFORMATION: Synthetic aptamer
<220> FEATURE:
<221> NAME/KEY: misc_feature
<223> OTHER INFORMATION: N represents a 2'OMe substituted nucleotide
<220> FEATURE:
<221> NAME/KEY: misc_feature
<222> LOCATION: (7)..(7)
<223> OTHER INFORMATION: n is a, c, g, or t

<400> SEQUENCE: 4
ggagganagt tcggtggctg ttcagggtct cctcc                              35

<210> SEQ ID NO 5
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<223> OTHER INFORMATION: N represents a 2'OMe substituted nucleotide
<220> FEATURE:
<221> NAME/KEY: misc_feature
<222> LOCATION: (16)..(16)
<223> OTHER INFORMATION: n is a, c, g, or t

<400> SEQUENCE: 5
ggaggatagt tcggtngctg ttcagggtct cctcc                              35

<210> SEQ ID NO 6
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<223> OTHER INFORMATION: N represents a 2'OMe substituted nucleotide
<220> FEATURE:
<221> NAME/KEY: misc_feature
<222> LOCATION: (22)..(22)
<223> OTHER INFORMATION: n is a, c, g, or t

<400> SEQUENCE: 6
ggaggatagt tcggtggctg tncagggtct cctcc                              35

<210> SEQ ID NO 7
<211> LENGTH: 37
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<223> OTHER INFORMATION: V represents locked deoxyadenosine, W
      represents locked deoxyguanosine, Y represents locked
      deoxythymidine and N represents locked deoxycytosine
<220> FEATURE:
<221> NAME/KEY: misc_feature
<222> LOCATION: (35)..(36)
<223> OTHER INFORMATION: n is a, c, g, or t

<400> SEQUENCE: 7
vwwvggatag ttcggtggct gttcagggtc tccynny                            37

<210> SEQ ID NO 8
<211> LENGTH: 37
<212> TYPE: DNA
<213> ORGANISM: Artificial Sequence
```

```
<220> FEATURE:
<223> OTHER INFORMATION: Synthetic aptamer
<220> FEATURE:
<221> NAME/KEY: misc_feature
<223> OTHER INFORMATION: Y represents locked deoxythymidine and N
      represents locked deoxycytosine
<220> FEATURE:
<221> NAME/KEY: misc_feature
<222> LOCATION: (35)..(36)
<223> OTHER INFORMATION: n is a, c, g, or t

<400> SEQUENCE: 8
aggaggatag ttcggtggct gttcagggtc tccynny                              37

<210> SEQ ID NO 9
<211> LENGTH: 37
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<223> OTHER INFORMATION: V represents locked deoxyadenosine and W
      represents locked deoxyguanosine

<400> SEQUENCE: 9
vwwvggatag ttcggtggct gttcagggtc tcctcct                              37

<210> SEQ ID NO 10
<211> LENGTH: 37
<212> TYPE: DNA
<213> ORGANISM: Artificial Sequence
<220> FEATURE:
<223> OTHER INFORMATION: Synthetic aptamer

<400> SEQUENCE: 10
aggaggatag ttcggtggct gttcagggtc tcctcct                              37

<210> SEQ ID NO 11
<211> LENGTH: 80
<212> TYPE: DNA
<213> ORGANISM: Artificial Sequence
<220> FEATURE:
<223> OTHER INFORMATION: Synthetic dimeric aptamer
<220> FEATURE:
<221> NAME/KEY: misc_feature
<223> OTHER INFORMATION: B represents spacer phosphoramadite 18

<400> SEQUENCE: 11
aggaggatag ttcggtggct gttcagggtc tcctcctbbb bbbaggagga tagttcggtg      60
gctgttcagg gtctcctcct                                                 80

<210> SEQ ID NO 12
<211> LENGTH: 82
<212> TYPE: DNA
<213> ORGANISM: Artificial Sequence
<220> FEATURE:
<223> OTHER INFORMATION: Synthetic dimeric aptamer
<220> FEATURE:
<221> NAME/KEY: misc_feature
<223> OTHER INFORMATION: B represents spacer phosphoramadite 18

<400> SEQUENCE: 12
aggaggatag ttcggtggct gttcagggtc tcctcctbbb bbbbaggag gatagttcgg       60 tggctgttca gggtctcctc ct                                              82

<210> SEQ ID NO 13
```

```
<211> LENGTH: 86
<212> TYPE: DNA
<213> ORGANISM: Artificial Sequence
<220> FEATURE:
<223> OTHER INFORMATION: Synthetic dimeric aptamer
<220> FEATURE:
<221> NAME/KEY: misc_feature
<223> OTHER INFORMATION: B represents spacer phosphoramadite 18

<400> SEQUENCE: 13
aggaggatag ttcggtggct gttcagggtc tcctcctbbb bbbbbbbba ggaggatagt    60 tcggtggctg ttcagggtct cctcct                                       86

<210> SEQ ID NO 14
<211> LENGTH: 90
<212> TYPE: DNA
<213> ORGANISM: Artificial Sequence
<220> FEATURE:
<223> OTHER INFORMATION: Synthetic dimeric aptamer
<220> FEATURE:
<221> NAME/KEY: misc_feature
<223> OTHER INFORMATION: B represents spacer phosphoramadite 18

<400> SEQUENCE: 14
aggaggatag ttcggtggct gttcagggtc tcctcctbbb bbbbbbbbb bbbaggagga    60 tagttcggtg gctgttcagg gtctcctcct                                   90

<210> SEQ ID NO 15
<211> LENGTH: 127
<212> TYPE: DNA
<213> ORGANISM: Artificial Sequence
<220> FEATURE:
<223> OTHER INFORMATION: Synthetic trimeric aptamer
<220> FEATURE:
<221> NAME/KEY: misc_feature
<223> OTHER INFORMATION: B represents spacer phosphoramadite 18

<400> SEQUENCE: 15
aggaggatag ttcggtggct gttcagggtc tcctcctbbb bbbbbaggag gatagttcgg    60
tggctgttca gggtctcctc ctbbbbbbbb aggaggatag ttcggtggct gttcagggtc   120
tcctcct                                                            127

<210> SEQ ID NO 16
<211> LENGTH: 172
<212> TYPE: DNA
<213> ORGANISM: Artificial Sequence
<220> FEATURE:
<223> OTHER INFORMATION: Synthetic tetrameric aptamer
<220> FEATURE:
<221> NAME/KEY: misc_feature
<223> OTHER INFORMATION: B represents spacer phosphoramadite 18

<400> SEQUENCE: 16
aggaggatag ttcggtggct gttcagggtc tcctcctbbb bbbbbaggag gatagttcgg    60
tggctgttca gggtctcctc ctbbbbbbbb aggaggatag ttcggtggct gttcagggtc   120
tcctcctbbb bbbbbaggag gatagttcgg tggctgttca gggtctcctc ct          172

<210> SEQ ID NO 17
<211> LENGTH: 37
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
```

<223> OTHER INFORMATION: Y represents locked deoxythymidine and N
      represents locked deoxycytosine
<220> FEATURE:
<221> NAME/KEY: misc_feature
<222> LOCATION: (35)..(36)
<223> OTHER INFORMATION: n is a, c, g, or t

<400> SEQUENCE: 17
aggaggatag ttcggtggct gttcagggtc tccynny                              37

<210> SEQ ID NO 18
<211> LENGTH: 85
<212> TYPE: DNA
<213> ORGANISM: Artificial Sequence
<220> FEATURE:
<223> OTHER INFORMATION: Synthetic dimeric aptamer
<220> FEATURE:
<221> NAME/KEY: misc_feature
<223> OTHER INFORMATION: D represents fluorescein isothiocyanate, B
      represents spacer phosphoramadite 18, N represents locked
      deoxycytosine, Y represents locked deoxythymidine
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t

<400> SEQUENCE: 18
dbaggaggat agttcggtgg ctgttcaggg tctccynnyb bbbbbbbagg aggatagttc     60
ggtggctgtt cagggtctcc ynnyb                                          85

<210> SEQ ID NO 19
<211> LENGTH: 129
<212> TYPE: DNA
<213> ORGANISM: Artificial Sequence
<220> FEATURE:
<223> OTHER INFORMATION: Synthetic trimeric aptamer
<220> FEATURE:
<221> NAME/KEY: misc_feature
<223> OTHER INFORMATION: D represents Cy3 phosphoramidite, B represents
      spacer phosphoramadite 18, N represents locked deoxycytosine, Y
      represents locked deoxythymidine
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (126)..(127)
<223> OTHER INFORMATION: n is a, c, g, or t

<400> SEQUENCE: 19
dbaggaggat agttcggtgg ctgttcaggg tctccynnyb bbbbbbbagg aggatagttc     60
ggtggctgtt cagggtctcc ynnybbbbbb bbggaggata gttcggtggc tgttcagggt    120 ctccynnyb                                                           129

<210> SEQ ID NO 20
<211> LENGTH: 173
<212> TYPE: DNA
<213> ORGANISM: Artificial Sequence
<220> FEATURE:
<223> OTHER INFORMATION: Synthetic tetrameric aptamer
<220> FEATURE:

```
<221> NAME/KEY: misc_feature
<223> OTHER INFORMATION: D represents Cy3 phosphoramidite, B represents
      spacer phosphoramadite 18, N represents locked deoxycytosine, Y
      represents locked deoxythymidine
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (126)..(127)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 20
dbaggaggat agttcggtgg ctgttcaggg tctccynnyb bbbbbbbagg aggatagttc      60
ggtggctgtt cagggtctcc ynnybbbbbb bbggaggata gttcggtggc tgttcagggt     120
ctccynnybb bbbbbggag gatagttcgg tggctgttca gggtctccyn nyb             173

<210> SEQ ID NO 21
<211> LENGTH: 52
<212> TYPE: RNA
<213> ORGANISM: Artificial Sequence
<220> FEATURE:
<223> OTHER INFORMATION: SYNTHETIC APTAMER TO BFGF, SEQUENCE 22B

<400> SEQUENCE: 21 cgucgagca ugcugagggu aacguacugg caagcucacc ucagcguagc ua              52

<210> SEQ ID NO 22
<211> LENGTH: 50
<212> TYPE: RNA
<213> ORGANISM: Artificial Sequence
<220> FEATURE:
<223> OTHER INFORMATION: SYNTHETIC APTAMER TO BFGF, SEQUENCE 28B

<400> SEQUENCE: 22 cgucgagca gcugagggua acguauaguc aagacaccuc aaguguagcu                 50

<210> SEQ ID NO 23
<211> LENGTH: 36
<212> TYPE: RNA
<213> ORGANISM: Artificial Sequence
<220> FEATURE:
<223> OTHER INFORMATION: SYNTHETIC APTAMER TO CD4, CLONE 8

<400> SEQUENCE: 23
cucagagaca gagcagaaac gacaguucaa gccgaa                               36

<210> SEQ ID NO 24
<211> LENGTH: 46
<212> TYPE: RNA
<213> ORGANISM: Artificial Sequence
<220> FEATURE:
<223> OTHER INFORMATION: SYNTHETIC APTAMER TO HER3 Sequence A30

<400> SEQUENCE: 24
cagcaaaguu gcguaugggu caucgcaggc acaugucauc ugggcg                    46
```

COMPOSITIONS AND METHODS FOR TREATING CANCER AND OTHER DISEASES

CROSS-REFERENCE TO RELATED APPLICATIONS

This application is a National Phase Application of PCT International Application No. PCT/US10/56881, International Filing Date Nov. 16, 2010, claiming priority of Provisional Patent Applications, 61/261,731, filed Nov. 16, 2009, and 61/394,736, filed Oct. 19, 2010.

GOVERNMENT SUPPORT

This work was supported in part by National Institutes of Health grants R01 CA55349, P01 33049 and R21 CA128406. The government may have certain rights to the invention.

BACKGROUND

Aptamers are short oligonucleotide sequences that can specifically bind to a wide range of target molecules, such as drugs, proteins, and other inorganic or organic molecules with high affinity and specificity (Tuerk C, Gold L. Systematic evolution of ligands by exponential enrichment: RNA ligands to bacteriophage T4 DNA polymerase. Science (1990) 249: 505-510; Ellington, A D, Szostak, J W. In vitro selection of RNA molecules that bind specific ligands. Nature (1990) 346: 818-822). Aptamer binding is based on the ability of small oligonucleotides (typically 40-100 mers) to fold into unique three-dimensional structures that can interact with a specific binding region of the target molecule. Aptamers have inherent advantages that merit application as therapeutic agents (Hnatowich D J, Nakamura K. The influence of chemical structure of DNA and other oligomer radiopharmaceuticals on tumor delivery. Curr. Opin. Mol. Ther. (2006) 8(2): 136-143): 1) the ability to withstand high heat and denaturants, 2) rapid chemical synthesis, 3) small size (10-20,000 daltons vs 150,000 daltons for antibodies), and 4) non-immunogenicity (Jayasena S D. Aptamers: an emerging class of molecules that rival antibodies in diagnostics. Clin. Chem. (1999) 45: 1628-1650). Typical monovalent aptamers are potentially limited by reduced retention times on the target cell and lack of crosslinking and subsequent activation of targets. Aptamer-based bivalent ligands, however, have been demonstrated to increase affinity and function compared to the monovalent versions; for example, bivalent aptamers were used to activate thrombin and T cells (Kim Y, Cao Z, Tan W. Molecular assembly for high-performance bivalent nucleic acid inhibitor. Proc. Natl. Acad. Sci. U S A. (2008) 105(15): 5664-5669; McNamara J O, Kolonias D, Pastor F, Mittler R S, Chen L, Giangrande P H, Sullenger B, Gilboa E. Multivalent 4-1BB binding aptamers costimulate CD8+ T cells and inhibit tumor growth in mice. Clin. Investi. (2008) 118: 376-386; Dollins C M, Nair S, Boczkowski D, Lee J, Layzer J M, Gilboa E, Sullenger B A. Assembling OX40 aptamers on a molecular scaffold to create a receptor-activating aptamer. Chem. Biol. (2008) 15(7): 675-682).

Recently, selection of a high affinity DNA aptamer (TD05) reactive with Burkitt's lymphoma was reported (Tang Z, Shangguan D, Wang K, Shi H, Sefah K, Mallikratchy P, Chen H W, Li Y, Tan W. Selection of aptamers for molecular recognition and characterization of cancer cells. Anal. Chem. (2007) 79: 4900-4907). At 4° C., TD05 binds to an epitope on B cell surface mIgM BCR, exclusively expressed on B cells and most B-cell lymphomas (Mallikaratchy P, Tang Z, Meng L, Shangguan D, Kwame S, Tan W. Aptamer directly evolved from live cells recognizes membrane bound immunoglobin heavy mu chain in Burkitt's lymphoma cells. Mol. Cell. Proteomics (2007) 6: 2230-2238). Aptamer TD05 is not useful in vivo, however, because of its lack of affinity and stability at physiological temperatures in human plasma. Moreover, it was not evident that TD05 could reach target B cells in vivo for diagnostic and therapeutic applications if the epitope was also present on circulating IgM, which is found in the plasma at 450-1500 mg/L (Furst D E. Serum immunoglobulins and risk of infection: how low can you go? Semin Arthritis Rheum. (2009) 39(1): 18-29). Although aptamers have the potential to be potent therapeutics for addressing a large number of conditions and diseases, such aptamers do not have characteristics that permit utility for administration to prevent or treat conditions or diseases, because of lack of persistence in circulation, susceptibility to nuclease attack, and poor affinity for the target molecule, among other disadvantages.

Aptamers with utility in vivo for treating cancers such as but not limited to B-cell lymphomas, as well as for the prevention or treatment of other conditions or diseases, are needed.

SUMMARY OF THE INVENTION

In one embodiment, aptamers are provided having efficacy for binding to target molecules in vivo or for treating cancer and other diseases. In another embodiment, improved or optimized aptamers are provided that have enhanced in vivo efficacy such as binding to the target molecule or enhancing anti-cancer activity or activity against other diseases, as compared to the unoptimized aptamer. In other embodiments, improvements to aptamers are provided selected from the group consisting of increased stability to serum nucleases, reduced binding to a soluble form of the target molecule, increased avidity, affinity or specificity to the target molecule on a cell surface, increased lifetime in circulation, or any combination of the foregoing. In other embodiments, pharmaceutical compositions of the aforementioned aptamers and improved aptamers are provided.

In another embodiment, the improved aptamer comprises at least one truncation of a nucleotide of the 5' end, a nucleotide of the 3' end, or both, of the unoptimized aptamer. In one embodiment, the truncation comprises at least one nucleotide truncated from either the 5' end, 3' end, or both. In one embodiment, the truncation comprises at least two nucleotides from either the 5' end, 3' end, or both. In one embodiment, the truncation comprises at least three nucleotides from either the 5' end, 3' end, or both. In one embodiment, the truncation comprises at least four nucleotides from either the 5' end, 3' end, or both. In one embodiment, the truncation comprises at least five nucleotides from either the 5' end, 3' end, or both. In one embodiment, the truncation comprises 1-5 nucleotides truncated from the 5' end, or, independently, 1-5 nucleotides truncated from the 5' end, or any combination of both. In one embodiment, the truncation comprises 1-10 nucleotides truncated from the 5' end, or, independently, 1-10 nucleotides truncated from the 5' end, or any combination of both.

In another embodiment the aptamer or improved aptamer comprises one or more non-natural nucleic acid bases. In one embodiment the non-natural nucleic acid base is a locked nucleic acid; locked nucleic acid bases are nucleoside analogues in which, in one embodiment, the ribose ring is "locked" by a methylene bridge connecting the 2'-O atom and the 4'-C atom. In another embodiment the non-natural nucleic acid base is a bicyclical furanose. In another embodiment the one or more non-natural bases are present in regions of the aptamer not involved in binding the target molecule. In another embodiment the one or more locked nucleic acids are present in the stem (duplex) portion of the aptamer structure.

In another embodiment the aptamer or improved aptamer comprises a polymer bound to the 3' end, to the 5' end, or the combination thereof. In one embodiment the polymer is polyethylene glycol. In one embodiment the polyethylene glycol is 6 ethylene glycol monomers in length. In other embodiments the polyethylene glycol is more than 6 ethylene glycol units, such as but not limited to 2-16 repeats of 6 ethylene glycol monomers. In other embodiments, the polyethylene glycol can have a molecular weight of from about 3,000 Da to about 300,000 Da, at either one or both ends of the aptamer. In other embodiments, the polyethylene glycol is about 3,000 to about 30,000 Da. In other embodiments, the polymer can be a copolymer of polyethylene glycol and polypropylene glycol, or carboxymethyl cellulose, dextran, polyvinyl alcohol, polyvinylpyrrolidone or polyproline. These are merely non-limiting examples.

In other embodiments, the aptamer or improved aptamer of the invention can have one or more of the aforementioned features. In one embodiment, the aptamer or improved aptamer has at least one truncation of a 5' or 3' end as described above and at least one locked nucleic acid as described above. In one embodiment, the aptamer or improved aptamer has at least one truncation of a 5' or 3' end as described above and at least polymer on a 5' or 3' end as described above. In one embodiment, the aptamer or improved aptamer has at least one locked nucleic acid as described above and at least one polymer on a 5' or 3' end as described above. In one embodiment, the aptamer or improved aptamer has at least one truncation of a 5' or 3' end as described above and at least one locked nucleic acid as described above. In one embodiment, the aptamer or improved aptamer has at least one truncation of a 5' or 3' end as described above, at least polymer on a 5' or 3' end as described above, and at least one locked nucleic acid as described above.

In another embodiment, the aptamer or improved aptamer is multivalent. In one embodiment multivalent comprises two aptamer monomers. In another embodiment multivalent comprises three aptamer monomers. In one embodiment multivalent comprises four aptamer monomers. In one embodiment multivalent comprises five aptamer monomers. In other embodiments, multivalent comprises more than four monomers. In another embodiment the multivalent aptamer is linear. In one embodiment, the two or more aptamer monomers are linked by a polymer. In another embodiment the polymer is polyethylene glycol. In another embodiment the polyethylene glycol linker between each aptamer is about 6 to about 96 ethylene glycol monomers in length. In another embodiment the polyethylene glycol linker between each aptamer is about 36 ethylene glycol monomers in length. In another embodiment the polyethylene glycol linker between each aptamer is about 48 ethylene glycol monomers in length. In another embodiment the polyethylene glycol linker between each aptamer is about 72 ethylene glycol monomers in length. In another embodiment the polyethylene glycol linker between each aptamer is about 96 ethylene glycol monomers in length. In another embodiment, each spacer of a multimeric aptamer comprising three or more aptamer monomers has the same length spacer. In another embodiment, each linker of a multimeric aptamer comprising three or more aptamer monomers is independently about 6 to about 96 ethylene glycol monomers in length. In other embodiments, the linkers are about 16.8 nm in length. In other embodiment, the length of the linkers in the multivalent aptamers are optimized for affinity and biological activity.

In other embodiments of the aforementioned multivalent aptamers, the aptamer monomer comprising the multivalent aptamer can have one or more of the aforementioned features of one or more locked nucleic acids, one or more truncations of a 5' or 3' end, or a polymer can be present on either the 5' end of the multivalent aptamer, the 3' end of the multivalent aptamer, or on both ends. Moreover, any combination of the aforementioned features may be present on a multivalent aptamer. For example, the multivalent aptamer can have at least one truncation of a 5' or 3' end of its monomeric aptamer components as described above and at least one locked nucleic acid in its monomeric aptamer components as described above. In another embodiment, the multivalent aptamer can have at least one truncation of a 5' or 3' end of its aptamer monomers as described above and at least polymer on a 5' or 3' end of the multivalent aptamer as described above. In another embodiment, the multivalent aptamer has at least one locked nucleic acid in each of the aptamer monomers as described above and at least one polymer on a 5' or 3' end of the mutimeric aptamer as described above. In one embodiment, the multivalent aptamer has at least one truncation of a 5' or 3' end of the aptamer monomer as described above, at least one polymer on a 5' or 3' end of the multivalent aptamer as described above, or on both, and at least one locked nucleic acid in each aptamer monomer as described above. In certain embodiments, the nucleotide portions of each aptamer monomer in the multivalent aptamer are the same, each optionally having the same at least one locked nucleic acid, the same at least one truncation, or both. In other embodiments each aptamer monomer in the multivalent aptamer may be different, independently having none or one or more of the aforementioned modifications.

In another embodiment, the improved aptamer comprises one of more of the aforementioned modifications to aptamer TD05 (SEQ ID NO:1).

In one embodiment, the aptamer or improved aptamer comprises one of more of the aforementioned modifications of an aptamer that binds to the B-cell receptor complex. In one embodiment, the aptamer or improved aptamer comprises one of more of the aforementioned modifications of an aptamer that binds to cell surface bound IgM. In another embodiment, the aptamer or improved aptamer binds a cell surface receptor, said binding therapeutically useful in treating a disease such as but not limited to cancer. In one embodiment the aptamer is TD05 (SEQ ID NO:1).

In another embodiment, the aptamer or improved aptamer can further comprise a chelator or a detectable label. In another embodiment the detectable label is a fluorophore. In another embodiment the aptamer or improved aptamer can carry a therapeutic molecule.

In another embodiment, the improved aptamer does not bind to soluble IgM.

In another embodiment, a method is provided for treating a cancer by administering to a subject in need thereof an aptamer or improved aptamer as embodied herein. In one embodiment the cancer is a B-cell cancer. In another embodiment, the B-cell cancer is a B-cell lymphoma. In another embodiment, the B-cell cancer is a non-Hodgkin's lymphoma. In other embodiments, the cancer is Burkett lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, or mantle cell lymphoma. In certain embodiments, the aptamer is a monomeric aptamer as that described as any one of SEQ ID NO:2-9. In other embodiments, the aptamer is a multimeric aptamer as described in any one of SEQ ID NO:11-20.

In other embodiments, the aptamer of any one of SEQ ID NO: 2-9 is provided. In other embodiments, the aptamer of any one of SEQ ID NO:11-20 is provided. In other embodiments, a pharmaceutical composition is provided comprising an aptamer of any one of SEQ ID NO:2-9 and a pharmaceutically acceptable carrier, diluent or excipient. In other embodiments, a pharmaceutical composition is provided comprising an aptamer of any one of SEQ ID NO:11-20 and a pharmaceutically acceptable carrier, diluent or excipient.

In other embodiments, an optimized monovalent aptamer or a multivalent aptamer has a therapeutic or diagnostic moiety bound thereto, such as but not limited to a toxic moiety, a radionuclide for imaging or therapy, a therapeutic molecule such as siRNA, a cytotoxin, or a chemotherpeutic agent. Pharmaceutical compositions comprising such conjugates and methods of treatment by administration to a subject in need thereof are embodied herein.

In other embodiments, a method is provided for treating cancer by administering to a subject in need thereof an aptamer or improved aptamer as embodied herein. Non-limiting examples of cancers treatable include lymphomas such as Hodgkin's lymphoma, non-Hodgkin's lymphoma, Burkitt's lymphoma, and other B-cell lymphomas, such as but not limited to diffuse large B cell lymphoma, follicular lymphoma, mucosa-associated lymphatic tissue lymphoma, small cell lymphocytic lymphoma, mantle cell lymphoma, mediastinal large B cell lymphoma, Waldenström macroglobulinemia, nodal marginal zone B cell lymphoma, splenic marginal zone lymphoma, intravascular large B cell lymphoma, primary effusion lymphoma and lymphomatoid granulomatosis; the treatment comprising administering to a subject in need thereof an improved or multimeric aptamer based on SEQ ID NO:1.

In other examples, aptamers targeted to molecules on other types of cancer or diseased cells can be optimized by modification of the monomer or multimerized in accordance with the teaching herein for use in treating a number of other conditions and diseases in which, for example, a cell surface molecule is the target of therapy. Diseases in which antibody therapies are successfully used to identify and kill or enhance the killing of a particular cellular population within the body are amenable to aptamer therapy, which aptamer therapy can be improved by modifying the aptamer in accordance with the optimization, multimerization, or combination methods as taught herein.

In other embodiments, a method is provided for treating an autoimmune disease by administering to a subject in need thereof an aptamer or improved aptamer as embodied herein. In certain embodiments, the autoimmune disease is lupus erythematosus, type I diabetes, rheumatoid arthritis, psoriasis, alopecia areata or anterior uveitis. In other embodiments, methods are provided for treating an autoimmune disease by administering to a subject in need thereof an aptamer of any one of SEQ ID NO: 2-9. In other embodiments, methods are provided for treating an autoimmune disease by administering to a subject in need thereof an aptamer of any one of SEQ ID NO:11-20.

Since the activation of the BCR in B-cells is directly related to B cell growth and function, the aptamers embodied herein derived from TD05 will be useful not only as modulators of B cell function, but modulators of function of other types of cells, as well as carriers of a therapeutic or diagnostic agent linked thereto. Therefore, such aptamers can have therapeutic activity in B cell cancers, auto-immune diseases, immune deficiency diseases, in immunosuppression, tolerization or in vaccination strategies. Generally, the aforementioned diseases and diagnostic applications related thereto are referred to as "B cell diseases".

In other embodiments, methods are provided for improving or optimizing an aptamer by the process of introducing into an unoptimized aptamer one or more of the following changes: incorporation of one or more locked nucleic acids, truncation at the 5' or 3' end, addition of a polymer to the 5' or 3' end, or multimerizing the aptamer into an oligomer comprising two or more monomeric aptamers, each of which optionally comprises at least one locked nucleic acid, truncation, or a 5' or 3' polymer on an end not linked to another aptamer. In one embodiment, the unoptimized aptamer is SEQ ID NO:1.

Thus, in certain embodiments, a multivalent aptamer having the sequence represented by SEQ ID NO:16, SEQ ID NO:15, SEQ ID NO:19 or SEQ ID NO:20 is provided. In other embodiments, a comprising the multivalent aptamer represented by SEQ ID NO:16, SEQ ID NO:15, SEQ ID NO:19 or SEQ ID NO:20 is provided. In other embodiments, a bivalent aptamer having the sequence represented by SEQ ID NO:11, SEQ ID NO:12, SEQ ID NO:13, SEQ ID NO:15 or SEQ ID NO:18 is provided. In other embodiments, a comprising the bivalent aptamer represented by SEQ ID NO:11, SEQ ID NO:12, SEQ ID NO:13, SEQ ID NO:15 or SEQ ID NO:18 is provided. In further embodiments, a monovalent aptamer is provided having the sequence represented by SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:17. In other embodiments, a comprising the monovalent aptamer represented by SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:17.

In other embodiments, an aptamer of any one of SEQ ID NO:1-19 further comprises a therapeutic or diagnostic agent. In another embodiment, the agent is a cytotoxic agent, a radionuclide, a fluorophore, an antibody, or a siRNA.

In further embodiments, a pharmaceutical composition is provided comprising any of the aptamer of SEQ ID NO:1-19, optionally further comprising a therapeutic or diagnostic agent, and a pharmaceutically acceptable carrier, diluent or excipient. In further embodiments, methods are provided for treating or diagnosing a B cell disease comprising administering to a subject in need thereof an aforementioned pharmaceutical composition. In certain embodiments, the B cell disease is cancer. In other embodiments, the B cell disease is an autoimmune disease, an immune deficiency disease, a disease benefitted by immunosuppression or as an adjunct to vaccination or tolerization.

BRIEF DESCRIPTION OF THE FIGURES

FIG. 7 is an investigation of binding as a function of temperature. (A) Flow cytometric analysis of TD05 aptamer binding to Ramos cells temperatures above 4° C. The fluorescence shift on the x-axis decreases to its background level at higher temperatures indicating that the $K_{off}$ is higher at temperatures higher than 4° C. (B) Predicted high affinity bulge secondary structure of TD05 changes with temperature to a low affinity stem-loop structure resulting dissociation of the complex.

DETAILED DESCRIPTION OF THE INVENTION

Figure 1:
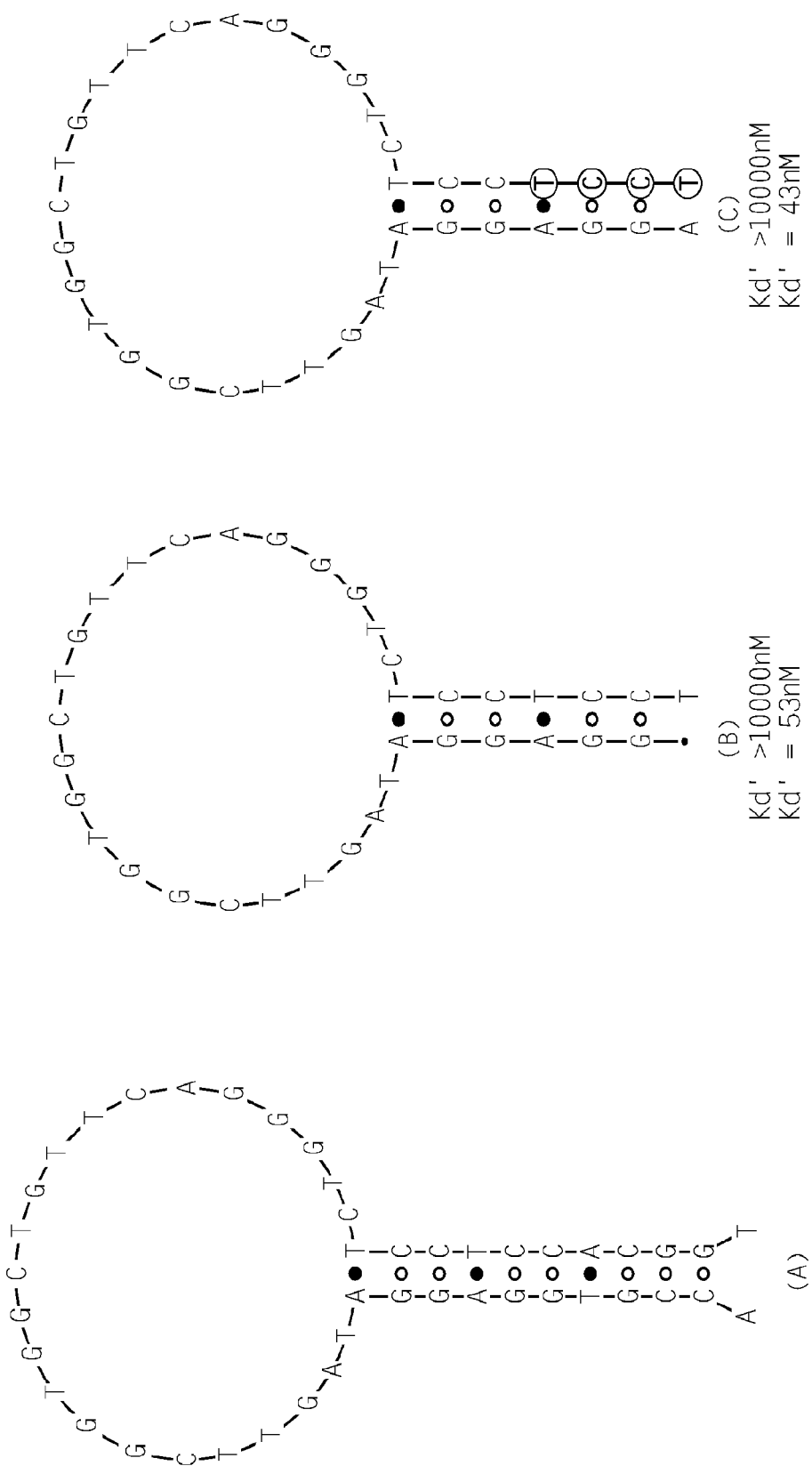
FIG. 1 shows the optimization of monomeric and multimeric aptamer scaffolds and their Bmax/2 (Kd') at 37° C. (top number) and at 4° C. (bottom number). A. Original (unoptimized) TD05 sequence, B. Truncated TD05.1, C. LNA modified TD05.1 (TD05.17), D. Bivalent TD05.17 (L-BVA.8S), E. Trivalent TD05.17 (L-TVA.8S), F. Tetravalent TD05.17 (L-TetVA.8S). The constructs were synthesized with PEG at the 5' and 3' ends; Cy3 or FITC was added at the 5' end. A circle around a nucleotide indicates a LNA base.
Figure 1:
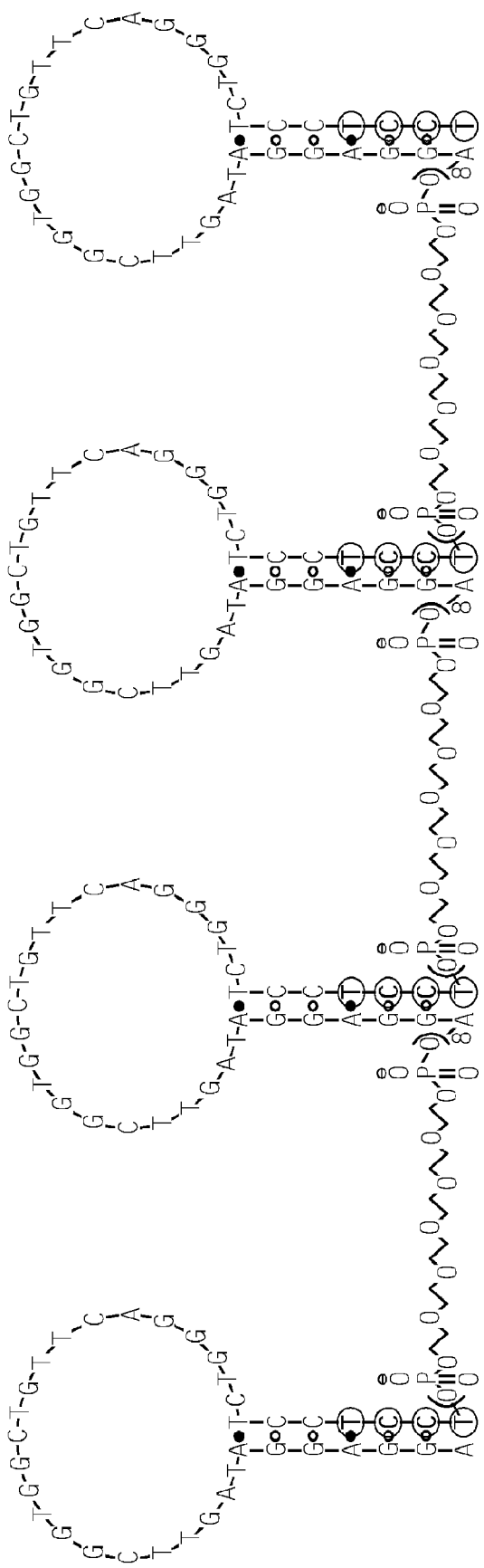

Non-Hodgkin's lymphomas (NHL) are the fifth most common type of cancer in the USA (Clarke C A, Glaser S L, Dorfman R F, Bracci P M, Eberle E, Holly E A. Expert review of non-Hodgkin's lymphomas in a population-based cancer registry: reliability of diagnosis and subtype classifications. Cancer Epidemiol Biomarkers Prey. (2004) 13(1): 138-143). While several effective chemotherapies and immunotherapy's are available, cures still elude most patients (Winter M C, Hancock B W. Ten years of rituximab in NHL. Expert Opin. Drug Saf. (2009) 8(3): 223-235). The addition of more selective strategies with monoclonal antibodies to cell surface targets such as CD20, CD22, or CD23 has improved outcomes and three antibodies to CD20 have been approved by the FDA to treat B cell NHL (Morris J C, Waldmann T A. Antibody-based therapy of leukaemia. Expert. Rev. Mol. Med. (2009) 11: e29). However, there are no approved agents that target the hallmark of the B cell, the B cell receptor (membrane Ig: mIgM) or BCR. Development of an antibody to mIgM is challenging because the unique epitopes are close to the cell surface and may be inaccessible to large antibody molecules. As noted above, long-term survival still eludes most patients with leukemia and non-Hodgkins leukemia (NHL). No approved therapies target the hallmark of the B cell, its mIgM, also known as the B cell receptor (BCR).

Aptamers are small oligonucleotides that can specifically bind to a wide range of target molecules and offer some advantages over antibodies as therapeutic agents. In one embodiment, the rational engineering of aptamer TD05 (SEQ ID NO:1; described in Tang Z, Shangguan D, Wang K, Shi H, Sefah K, Mallikratchy P, Chen H W, Li Y, Tan W. Selection of aptamers for molecular recognition and characterization of cancer cells. Anal. Chem. (2007) 79: 4900-4907) by optimizing the monomeric form, and in another embodiment, preparing multimeric forms reactive with the BCR, produced new therapeutic agents with physiologic activity in vivo that may be useful in numerous biomedical applications. In certain embodiments, systematic truncation of the aptamer TD05 coupled with modification with locked nucleic acids (LNA) increased conformational stability and nuclease resistance. Activity was further increased by dimerization and optimization of the linker length between the aptamer monomers. Trimetric and tetrameric versions with optimized polyethylene glycol (PEG) linker lengths exhibited high avidity at physiological temperatures both in vitro and in vivo. Competition and protease studies showed that the multimeric, optimized aptamer bound to membrane-associated human mIgM, but not with soluble IgM in plasma, allowing the potential of targeting leukemias and lymphomas in vivo. The B cell specificity of the multivalent aptamer was confirmed on lymphoma cell lines and fresh clinical leukemia samples. The chemically engineered aptamers, with significantly improved kinetic and biochemical features, unique specificity, and desirable pharmacological properties, and in particular the trimeric and tetrameric forms, may be useful in numerous biomedical applications. These results described in the examples indicate that the methods embodied herein and the improved properties of aptamers as described herein can be employed using other monomeric, unoptimized aptamers to create therapeutically useful agents to address a large number of diseases or enhance immune-based therapies.

The teaching herein are applicable to DNA based as well as RNA based aptamers.

To address the needs for aptamers that have utility in vivo and thus produce aptamers with potential medical applications, one particular aptamer (TD05; SEQ ID NO:1) that targets a B cell surface epitope, was studied as a non-limiting example; the findings described herein applicable to other aptamers that target other cell surface molecules including receptors or other proteins located on or in cells, and thus applicable to addressing numerous other diseases. Other aptamers can be identified in the literature, such as those described at the website http://aptamer.icmb.utexas.edu/index.php, incorporated herein by reference. Non-limiting examples of some unoptimized monomeric aptamer sequences targeting molecules include: fibroblast growth factor 2, basic, Sequence 22B: C CUGUCGAG-CAUGCUGAGGGUAACGUACUGGCAAGCU-CACCUCAGCGUAGCUA (SEQ ID NO:21) and Sequence 28B: CUGUCGAG-CAGCUGAGGGUAACGUAUAGUCAAGA-CACCUCAAGUGUAGCU (SEQ ID NO:22; Jellinek, D. et al. High-affinity RNA ligands to basic fibroblast growth factor inhibit receptor binding. Proc. Natl Acad. Sci. USA 90, 11227-11231 (1993); CD4 : Sequence Clone 8: CUCA-GAGACAGAGCAGAAACGACAGUUCAAGCCGAA (SEQ ID NO:23) (Jellinek, D. et al. High-affinity RNA ligands to basic fibroblast growth factor inhibit receptor binding. Proc. Natl. Acad. Sci. USA 90, 11227-11231 (1993) and; HER3 Sequence A30: CAGCAAAGUUGCGUAUGGGU-CAUCGCAGGCACAUGUCAUCUGGGCG (SEQ ID NO:24; Hen, C. H. et al Inhibition of heregulin signaling by an aptamer that preferentially binds to the oligomeric form of human epidermal growth factor receptor-3. Proc. Natl Acad. Sci. USA 100, 9226-9231 (2003)).

In the examples shown below and exemplary of the methods for optimizing aptamers and providing compositions and pharmaceutical compositions thereof, first, TD05 was optimized by truncation, and then further optimized by introducing non-naturally occurring nucleic acids, in this non-limiting example locked nucleic acids (LNA), to increase nuclease resistance and conformational stability. The construct was additionally redesigned into bivalent, trivalent and tetravalent multimers in order to improve the affinity, with the intent to create an agent that could crosslink the BCR, which might have the biological effect of modulating the cell surface expression of the BCR, internalizing the complex, or activating or deactivating signaling pathways (Irish J, Czerwinski D K, Garry P, Nolan X R, Levy R. Altered B-cell receptor signaling kinetics distinguish human follicular lymphoma B cells from tumor infiltrating nonmalignant B cells. Blood. (2006) 108: 3135-3142; Herzog S, Reth M, Jumaa H. Regulation of B-cell proliferation and differentiation by pre-B-cell receptor signaling. Nat. Rev. Immunology. (2009) 9: 195-205). A further optimization applicable to the monomer or multimeric forms is the addition to one or both ends of the aptamer a polymer, such as but not limited to polyethylene glycol.

The rational engineering of multivalent aptamer scaffolds embodied herein show higher thermal and nuclease stability, conformational stability, improved kinetic and biochemical properties at physiological temperatures, e.g., about 35° C. to about 42° C., optimally about 37° C. in humans, and thus potential as therapeutically useful agents to address a large number of diseases such as but not limited to cancer and autoimmune diseases.

As described herein, aptamers embodied herein can comprise one of more of the features described herein, such as truncation, multimerization, presence of a polymeric linker or linkers, presence of one or more non-natural nucleic acid bases, or a polymer at the 3' or 5' end, or both, or any combination of any of the foregoing. For example, an aptamer may be multimeric, having two, three, four, five, or more aptamer monomers. The multimerization may be provided by a polymeric linker between the subunits, such as polyethylene glycol by way of non-limiting example of a polymer. The monomeric or multimeric aptamer may have one or more non-natural nucleic acid base therein. In other embodiments, the monomeric or multimeric aptamer may have a polymer at one or both ends. In certain embodiments, the aptamer may be a multimer with polymer linkers and non-natural nucleic bases. In certain embodiment, "improved aptamer" "optimized aptamer" "modified aptamer" "new aptamer" or "derived aptamer" refers to a "known", "original", or "unoptimized" aptamer that is improved in one or more features by following the teachings herein, such as but not limited to incorporation of one or more of the features mentioned above. An aptamer with a single stem-loop structure or a single target molecule binding site is referred to herein as a monomer or monomeric, univalent or single aptamer. An aptamer product comprising two or more single aptamers is referred to herein as a multimeric, oligomeric, multivalent or polymeric aptamer, including syntactically similar terminologies such as multimer, oligomer and polymer. Dimer or dimeric refers to a product consisting of two aptamer monomers; trimer or trimeric, three; and tetramer or tetrameric, four. A spacer or linker, terms used synonymously, refer to the polymer that joins or links two or more aptamers in a multivalent aptamer. An aptamer is an improved, modified, optimized or derived aptamer if it comprises at least one modification described herein and embodies at least one improvement described herein, such as but not limited to enhanced efficacy for binding to a target molecule in vivo for treating or diagnosing cancer or another disease, increased stability to serum nucleases, reduced binding to a soluble form of the target molecule, increased avidity, affinity or specificity to the target molecule on a cell surface, increased lifetime in circulation, or any combination of the foregoing. In other embodiments, the aptamer is not a prior known aptamer but is designed to bind to a particular target molecule and incorporates at least one of the features described herein: locked nucleic acid, truncation as compared to other known aptamers, polymer at the 5' or 3' or both ends, or multimerization, or any combination thereof.

In certain embodiments, the improvement in biological activity is achieved by multimerizing the aptamer, such as multimerizing a new univalent aptamer molecule or multimerizing a known univalent aptamer. In other embodiments, a multimer of three or four univalent aptamers provides significantly increased biological activity. Further improvement in biological activity is achieved by a combination of multimerization and adding a polymer to the 5' or 3' end of the multimeric aptamer, or to both ends. In other embodiments further improvement in biological activity is achieved by modifications to the aptamer monomers comprising the multimeric aptamer, such as truncation or changing certain bases to locked nucleic acids.

As mentioned above, the TD05 aptamer, after optimization by truncation to TD05.1, was additionally redesigned into bivalent, trivalent and tetravalent scaffolds in order to further increase the affinity, reduce off-rates, and possibly to create an agent that could crosslink the BCR, which might have the biological effect of modulating the cell surface expression of the BCR, internalizing the complex, or activating or deactivating its signaling pathways. The bivalent aptamer was also used to assess the specificity towards the IgM epitope and to investigate the ability of binding in the presence of excess soluble IgM. Since the activation of the BCR in B-cells is directly related to B cell growth and function, these aptamers are expected to be useful not only as modulators of B cell function, but modulators of function of other types of cells, as well as carriers of a therapeutic agent linked thereto. Therefore, such aptamers can have therapeutic activity in B cell cancers, autoimmune diseases, immune deficiency diseases, in immunosuppression, tolerization or in vaccination strategies. In other embodiments, the aptamers and improved aptamers embodied herein can be used therapeutically in any disease or condition in which binding to a particular target molecule in the body is of therapeutic advantage. In one embodiment the target molecule is on a cell surface. In other embodiments the target molecule is inside a cell and a means for cellular penetration or permeation included in the composition or an agent for delivery across a cell membrane covalently or noncovalently bound to the aptamer. In other embodiments, the improved aptamers described herein are used to deliver other molecules to particular target molecules on or in cells, such as imaging reagents, cytotoxins, radionuclides, and siRNA molecules, to name a few. The enhanced affinity, binding, and biological activity of the improved aptamers embodied herein are useful if the aptamer is directly or indirectly responsible for the prevention or treatment of a condition or disease, or the identification or diagnosis of a condition or disease or the risk therefor. Moreover, conjugates of aptamers embodied herein to other moieties including but not limited to scaffolds, sugars, proteins, antibodies, polymers and nanoparticles are fully embodied herein.

Subsequently, dimers, trimers and tetramers of aptamer TD05 were prepared after optimization of the monomer by truncation and including LNAs in the stem region (TD05.17), using, in one embodiment, a linker of 48 ethylene glycol monomers. Further increase in binding affinity was observed. Polyvalent aptamers prepared according to this embodiment are likewise useful for the same biological activities as mentioned above. Polymeric linkers comprising of from about 48 to about 96 ethylene glycol monomers were found the be useful in providing polyvalent aptamers with increased affinity and biological activity. Selection of linker lengths to optimize activity can be carried out by following the teachings herein.

Nonlimiting examples of known aptamers that may be rendered useful for medical use as described herein include, in addition to those mentioned above (SEQ ID NOS:21-24), aptamers targeting tenascin C for treating cancer, aptamers targeting PSMA for treating prostate cancer, aptamers targeting PTK7 for treating cancer, aptamers targeting thrombin for treating coagulopathies, aptamers targeting OX40 for treating inflammation and autoimmune diseases, aptamers targeting PDGF for treating retinopathies, aptamers targeting C5 for treating macular degeneration, aptamers targeting factor IXa for treating coagulopathies, aptamers targeting VEGF for treating retinopathies, and aptamers targeting tissue factor pathway inhibitor for treating coagulopathies, to name just a few non-limiting examples.

Furthermore, the improved aptamers embodied here, in addition to direct therapeutic benefits by binding to target molecules on or in cells, can be used to deliver toxic moieties, radionuclides for imaging or therapy, or therapeutic molecules such as siRNA, cytotoxins, and chemotherpeutic agents. Any such uses of the improved aptamers described herein are embodied herein. Such uses of aptamers are described in Ray P and White RR. (2010) Aptamers for targeted drug delivery. Pharmaceuticals 3:1761-78.

A discussion of each of the modifications ensues. As noted above, an aptamer of the invention can incorporate one or more of such modifications, and in the case of a multimeric aptamer, each monomer unit may have the same or different modifications from the others.

Locked Nucleic Acids. Locked nucleic acids (LNAs) are a class of nucleic acid analogues in which the ribose ring is "locked" by a methylene bridge connecting the 2'-O atom and the 4'-C atom. LNA nucleosides contain the common nucleic acid bases (T, C, G, A, U and mC) and are able to form base pairs according to standard Watson-Crick base pairing rules. By "locking" the molecule with the methylene bridge the LNA is constrained in the ideal conformation for Watson-Crick binding. When incorporated into a DNA oligonucleotide, LNA therefore makes the pairing with a complementary nucleotide strand more rapid and increases the stability of the resulting duplex. LNAs are described in U.S. Pat. Nos. 6,268,490, 6,770,748, 6,639,059, and 6,734,291. LNAs can be purchased from Exiqon Life Sciences, Vedbaek, Denmark.

Other examples of non-natural bases that can be incorporated into the aptamers embodied herein include morpholinos and 2'-substituted nucleotides to provide resistance to nucleases. Substitution at the 2' position of the ribose sugar with either a fluoro- (F), amino- ($NH_2$) or O-methyl ($OCH_3$) group of any nucleic acid can be used to increase the nuclease resistance.

In another embodiment, the one or more non-natural bases such as LNAs are introduced into one or more regions of the aptamer not involved in binding the target molecule, such as the stem (duplex) region of the aptamer. In one embodiment, after truncation of an unoptimized aptamer as described below, LNAs replace from one to more than one of the 5' terminal or 3' terminal bases, or both, such as shown in SEQ ID NO: 7, 8 and 9, where the terminal 4 bases of either or both termini of the aptamer are replaced with their corresponding LNAs. In certain embodiments, only one nucleotide of a pair of nucleotides (AT or CG) but not both is replaced with a non-natural base at each location in a duplex region of the aptamer. These modifications increase the affinity of the aptamer as a monomer, and when incorporated into a multimeric aptamer, result in increased affinity and in vivo biological activity.

In one embodiment, LNA bases are introduced in a favorable combination by substituting pyrimidines on the stem of the aptamer monomer. In certain embodiments, the substitution of the purines in the stem may impaired binding, suggesting that the binding site of the aptamer is affected by these residues. However, as will be readily determined by the skilled artisan without undue experimentation, the appropriate substitution of bases with LNAs will provide a stabilized the structure leading to a higher affinity constant than the original structure.

Truncation. The biological activity of an unoptimized aptamer can be increased by deleting bases from the 5' or 3' termini or both. For example, deleting two or five terminal bases from each end of SEQ ID NO:1 results in aptamers, SEQ ID NO:2 and 3, respectively, with higher affinity. Using such a truncated aptamer monomer in preparing a multimeric aptamer results in a product with increased biological activity including in vivo activity.

Polymeric 5' or 3' Ends. Addition of a polymer such as but not limited to polyethylene glycol to the 5' or 3' end of a monomeric or multimeric aptamer can increase the biological activity. For example, addition of an 8-mer of ethylene glycol to the termini of multimeric aptamer SEQ ID NOs:15 and 16 results in higher affinity aptamers SEQ ID NO:19 and 20, respectively. Polymers such as but not limited to polyethylene glycol, polylactic acid, and polylysine can be used, as well as copolymers of polyethylene glycol and polypropylene glycol; carboxymethyl cellulose; dextran; polyvinyl alcohol; polyvinylpyrrolidone or polyproline. By using polymers with phosphoramidite moieties, such as are available from Glen Research, simplified synthesis of the aptamers with polymeric ends can be achieved. In some cases a fluorescent moiety such as cyanine or fluorescein can be incorporated into the aptamer for quantification purposes. Useful spacer reagents and labeling reagents include Spacer Phosphoramidite 18 ("sp18"), 18-O-dimethoxytritylhexaethyleneglycol,1-[(2-cyanoethyl)- (N,N-diisopropyl)]-phosphoramidite; Amino-Modifier C6 dT, 5'-dimethoxytrityl-5-[N-(trifluoroacetylaminohexyl)-3-acrylimido]-2'-deoxyuridine,3'-[(2-cyanoethyl)-(N,N-diisopropyl)]-phosphoramidite; 5'-Fluorescein Phosphoramidite ("FITC"), 6-(3',6'-dipivaloylfluoresceinyl-6-carboxamido)-hexyl-1-O-(2-cyanoethyl)-(N,N-diisopropyl)-phosphoramidite; and Cy3 Phosphoramidite ("Cy3"), 1-[3-(4-monomethoxytrityloxy)propyl]-1'-[3-[(2-cyanoethyl)-(N,N-diisopropyl)phosphoramidityl]propyl]-3,3,3',3'-tetramethylindocarbocyanine chloride.

Dimers. As noted herein, providing a dimer of unoptimized or optimized (by truncation, inclusion of LNAs, or both) aptamer monomers produces a dimeric product with enhanced properties, such as increased affinity for and binding to a target molecule, and increased biological activity. In certain embodiments, two aptamer monomers can be linked by a polymeric spacer to provide a dimeric aptamer, such as SEQ ID NOs: 11-14, and 18. As noted in the examples below, a number of spacers each comprising 6 ethylene glycol monomer units, provided by the reagent spacer phosphoramidite 18 ("sp18"), provided optimal binding for a dimeric aptamer. For example, in the dimeric aptamer, a spacer comprising sixteen sp18 units (total of 96 ethylene glycol monomers) enhanced affinity. Other spacer lengths can be easily optimized for particular aptamers, such as but not limited to from about one to about 16 repeats of a six-ethylene glycol monomer unit, such as sp18 as described herein. In other embodiments 6, 8, 12 or 16 units of six-ethylene glycol monomers are provided as spacers. This provides spacers of from about 6 to about 96 ethylene glycol units. In other embodiments the spacer is a copolymer of polyethylene glycol and polypropylene glycol; carboxymethyl cellulose; dextran; polyvinyl alcohol; polyvinylpyrrolidone or polyproline. In other embodiments each spacer is from about 12 to about 34 nm in length, such as but not limited to 12.6, 16.8, 25.2 or 33.6 nm in length. Such dimeric aptamers, as noted above, can optionally incorporate one or more of the optimization features to the monomer aptamers comprising the dimer, and in addition can have a polymer bound to the 5' or 3' end, or both.

Trimers. As noted herein, providing a trimer of unoptimized or optimized aptamer monomers, or any combination thereof, produces a product with enhanced properties, such as increased affinity for and binding to a target molecule and increased biological activity including in vivo biological activity. As described in the examples below, a trimeric product of optimized aptamer monomers (SEQ ID NO: 15) was shown to have high binding affinity at physiological temperature, and increased stability in human serum. For example, spacers comprising eight sp18 units (total of 48 ethylene glycol monomers) between each aptamer provided enhanced affinity in the trimer. Other spacer lengths can be easily optimized for particular aptamers, such as but not limited to from about one to about 16 repeats of a six-ethylene glycol monomer unit, such as sp18 as described herein. In other embodiments 6, 8, 12 or 16 units of six-ethylene glycol monomers are provided as spacers. This provides spacers of from about 6 to about 96 ethylene glycol units. In other embodiments the spacer is a copolymer of polyethylene glycol and polypropylene glycol; carboxymethyl cellulose; dextran; polyvinyl alcohol; polyvinylpyrrolidone or polyproline. In other embodiments each spacer is from about 12 to about 34 nm in length, such as but not limited to 12.6, 16.8, 25.2 or 33.6 nm in length. Such trimeric aptamers, as noted above, can optionally incorporate one or more of the optimization features to the monomer aptamers comprising the trimer, and in addition can have a polymer bound to the 5' or 3' end, or both. Such trimeric aptamers provide increased biological activity and utility as compared to dimeric or monomeric aptamers.

Tetramers. As noted herein, providing a tetramer of unoptimized or optimized aptamer monomers, or any combination thereof, produces a product with enhanced properties, such as increased affinity for and binding to a target molecule and increased biological activity. For example, spacers comprising eight sp18 units (total of 48 ethylene glycol monomers) between each aptamer provided enhanced affinity in the tetramer. Other spacer lengths can be easily optimized for particular aptamers, such as but not limited to from about one to about 16 repeats of a six-ethylene glycol monomer unit, such as sp18 as described herein. In other embodiments 6, 8, 12 or 16 units of six-ethylene glycol monomers are provided as spacers. This provides spacers of from about 6 to about 96 ethylene glycol units. In other embodiments the spacer is a copolymer of polyethylene glycol and polypropylene glycol; carboxymethyl cellulose; dextran; polyvinyl alcohol; polyvinylpyrrolidone or polyproline. In other embodiments each spacer is from about 12 to about 34 nm in length, such as but not limited to 12.6, 16.8, 25.2 or 33.6 nm in length. A tetrameric aptamer product (SEQ ID NO:16) was shown to recognize the target binding epitope on Ramos cells in vivo. Such tetravalent aptamers, as noted above, can optionally incorporate one or more of the optimization features to the monomer aptamers comprising the tetramer, and in addition can have a polymer bound to the 5' or 3' end, or both. Such tetrameric aptamers provide increased biological activity and utility as compared to trimeric, dimeric or monomeric aptamers as described above.

Higher oligomers. Following the teachings provided herein, oligomeric aptamers incorporating more than four aptamer monomers, unoptimized or optimized in accordance with the embodiments described herein, and in any combination thereof, can be prepared to provide increased affinity for and binding to a target molecule, as well as increased biological activity including activity in vivo. Such oligomeric aptamers incorporating, by way of non-limiting example, 5-10 aptamer monomers, are fully embraced by the teachings herein. Spacer lengths can be easily optimized for particular aptamers, such as but not limited to from about one to about 16 repeats of a six-ethylene glycol monomer unit, such as sp18 as described herein. In other embodiments 6, 8, 12 or 16 units of six-ethylene glycol monomers are provided as spacers. This provides spacers of from about 6 to about 96 ethylene glycol units. In other embodiments the spacer is a copolymer of polyethylene glycol and polypropylene glycol; carboxymethyl cellulose; dextran; polyvinyl alcohol; polyvinylpyrrolidone or polyproline. In other embodiments each spacer is from about 12 to about 34 nm in length, such as but not limited to 12.6, 16.8, 25.2 or 33.6 nm in length.

Conjugates. As noted above, a diagnostic or therapeutic moiety can be conjugated to an aptamer embodied herein to provide additional biological activity, such as for diagnosing, preventing, or treating a condition or disease. In one embodiment a diagnostic moiety such as a detectable label, fluorescent, radioactive, etc., can be bound to the aptamer, and imaging, immunohistochemistry, or other invasive or non-invasive methods used to identify the location(s) and extend of binding of the conjugate to locations within the body. For therapeutic uses, a cytotoxic agent such as a chemotherapeutic agent, radioactive moiety, toxin, antibody, small interfering RNA (siRNA) or other molecule with therapeutic activity when delivered to cells expressing a molecule to which the aptamer is targeted, may be used to enhance the therapeutic activity of the aptamer or provide a biological activity where the aptamer is providing the targeting activity. Moreover, other conjugates to the aptamers described herein are contemplated, such as but not limited to scaffolds, sugars, proteins, antibodies, polymers, and nanoparticles, each of which have art-recognized therapeutic or diagnostic utilities and can be targeted to particular sites in vivo using an aptamer embodied herein.

The preparation of the monomeric and polymeric aptamers embodied herein as well as the methods for evaluation in vitro and in vivo can be achieved by following the descriptions provided herein including those in the examples below, as well as in the literature referred to herein which is fully incorporated herein by reference. For example, DNA oligonucleotide sequences can be chemically synthesized using standard solid phase phosphoramidite chemistry on, for example, an ABI394 DNA synthesizer using either a 0.2 µmole or 1 mole scale. Synthesis can include attaching a fluorophore at the 5' end. The completed DNA sequences are then de-protected, and the crude product purified using, for example HPLC (Beckman Coulter System Gold Bioessential 125/168 diode-array detection instrument) equipped with a C-18 column (Dyanamax 250×10 mm, Varian) using 0.1M TEAA as the mobile phase. The length of each DNA construct can be confirmed using 10%-TBE urea polyacrylamide gel electrophoresis. Full length DNA can be quantified by measuring the absorbance at 260 nm and absorbance of the corresponding dye at the 5' position using a Cary Bio-100 UV-Visible spectrophotometer (Varian). Sequences used in NMR experiments can be further dialyzed overnight with 0.5 mM $NaHPO_4$ buffer using a MWCO 1000 Da dialysis bag.

Methods for administration of the aptamers embodied herein and compositions comprising the aptamers to a subject in need of therapy or at risk of developing a condition or disease preventable or treatable by the aptamers embodied herein, are also described herein. For example, aptamer can be administered parenterally in a solution comprising excipients, diluents or carriers, such as described further below. Aptamer products can be prepared for clinical use, filter sterilized and lyophilized from a buffer containing sugars such as sucrose and D-mannitol to stabilize the aptamer and provide an isotonic solution upon reconstitution before administration. The foregoing description is also applicable to embodied aptamers used for imaging or diagnostic purposes or procedures.

By way of example of the B-cell receptor as a non-limiting representative of a target of an aptamer embodied herein, the BCR is a unique feature of cells of B-cell lineage, including most B-cell NHL. Therefore, the BCR is an attractive therapeutic target for lymphoma or disorders of the immune system. Approaches to this target, however, have been limited by the lack of an appropriate reagent that could selectively bind to an epitope on the BCR that was not also present on the circulating, soluble IgM, which is found at high concentrations in human plasma. One difficulty in identifying an antibody-based reagent to the mIgM may be that the unique epitopes near the cell surface are inaccessible to large antibody molecules. Since the activation of the BCR in B-cells is directly related to B-cell growth and function, the multivalent forms of agents that specifically bind to the BCR, such as the aptamers described here, have potential utility not only as vehicles for therapeutic cargo, but also as modulators of B cell function. Therefore, aptamers might have therapeutic applications in cancer, auto-immune diseases, immune deficiency diseases, in immunosuppression or in vaccination strategies.

In a further embodiment, multimeric compositions as described here can also be used as a biological signal inducer of cell death pathways via BCR crosslinking. The BCR is comprised of two identical heavy chains and two identical light chains covalently linked by di-sulfide bridges, complexed with accessory molecules CD79A and CD79B. These accessory molecules express cytoplasmic immuno-receptor tyrosine based activation motifs (ITAMS). ITAMS are phosphorylated upon BCR activation and three PTKs (Lyn, Syk, and Btk) and one PTP (SHP-1) are involved in signal transduction and activation of down-stream signaling molecules. Signaling events that originate from the BCR either can promote differentiation or promote programmed cell death on a specific cell type. The outcome of the BCR signaling is depending on the cell type, extent of BCR crosslinking, affinity of the antibody, and which pathway is being activated.

A previously described aptamer, TD05, appeared to bind to the mIgM, but was not able to bind its target under physiologic conditions, nor was its selectivity for the mIgM vs soluble IgM known. So far, attempts to develop antibodies for mIgM have been limited due to interactions with the soluble versions (Thielemans K, Maloney D G, Meeker T, Fujimoto J, Doss C, Warnke R A, Bindl J, Gralow J, Miller R A, Levy R. Strategies for production of monoclonal anti-idiotype antibodies against human B cell lymphomas. J. Immunol. (1984) 133(1): 495-501). The optimized aptamers exemplified here are unique due to their interaction with the mIgM but not with soluble IgM, significantly increasing the potential therapeutic application as a BCR cross-linker or as a drug delivery agent.

In one embodiment, rational engineering was used to prepare a new aptamer, derived from TD05, that can selectively recognize mIgM under physiological conditions. The teachings herein can be applied to improving other aptamer molecules to provide or increase its therapeutic utility. Here, improving the aptamer TD05 rendered it suitable for in vivo applications by addressing issues pertaining to specificity, affinity, and in vivo stability. As will be shown in the examples below, first, truncation of the aptamer TD05 resulted in improved binding, presumably by creating a compact fold which better fit with the epitope. Second, in order to increase the structural stability, LNA bases were introduced in a favorable combination by substituting pyrimidines on the stem. The substitution of the purines in the stem has impaired binding, suggesting that the binding site of the aptamer is affected by these residues. However, the pyrimidine substitution stabilized the structure leading to a higher affinity constant than the original structure. Since LNAs are resistant to nuclease digestion, LNA modification of the stem not only stabilizes the secondary structure by forming a strong stem, but also will increases the stability against nuclease attack. Third, PEGylation of the aptamer ends was employed to improve stability and pharmacologic performance. Fourth, the multimerization of monomer significantly increase the avidity at physiological temperature. In various embodiments herein, one or more of the foregoing modifications of an aptamer will enhance therapeutic activity, or in certain cases, convert a aptamer lacking in vivo biological activity into an active agent useful therapeutically or diagnostically. The teachings provided here will be readily understood by the skilled artisan and applied to the creation or improvement of aptamers of therapeutic value to address a wide range of medical needs for humans, as well as livestock, domesticated animals and pets.

As shown in the examples below, using a linear assembly, novel multimeric scaffolds with increased avidity are provided. These constructs were readily synthesized using PEG phosphoramidite and automated DNA synthesis to synthesize the multivalent scaffold. The direct synthesis minimized tedious and low yield bio-conjugation reactions and polydispersed products. The use of long flexible linkers aided in promoting the proper conformation and avoided loss of binding due to steric hindrance.

The design of a multivalent scaffold for multiple targets is often challenging, due to complexity of the binding patterns. As described herein, the binding of low valency scaffolds mainly depends on the protein density on the cell surface. The dependence on the cell surface density on binding is problematic for the optimization of the linker lengths. Linker lengths from 12.6 nm to 25.2 nM were found to not show a significant difference in the binding constant at 4° C., which may be due to different patterns of binding in which the binding of the ligands on either one site or in two different sites in two different proteins can accommodate the aptamer. The changes of the avidity at 37° C. are more significant with increasing valency. While the avidity increased with increased valency, the nature of the interactions with variable linkers will likely vary with mIgM density on the membrane; the skilled artisan will readily determine for a particular target the construction of the aptamer to optimally interact therewith. The combination of truncation, LNA modification and multimerization has shown additive effects in making the avidity of the tri- and tetrameric scaffolds more than 40-fold higher than the corresponding original monomeric aptamer. As before, the skilled artisan can readily create a combination of valency, non-natural nucleic acid bases and truncation of known monomeric aptamers, or create de novo an aptamer, that has sufficient avidity to be therapeutically useful.

The observed lack of binding of the original aptamer TD05 at 37° C. may be due to changes of the aptamer structure with increasing temperature. In one embodiment, the bi-loop structure (FIG. 7) instead of a stem-loop region in TD05 melts with increasing temperature, yielding a low affinity structure B at physiological temperatures that cannot compete with the thermal instability resulting in dissociation of the complex. Moreover, it has been reported that, the lateral angle of the mIgM in the membrane changes with temperature due to changes of the hydrocarbon structure of the membrane of B-lymphocytes (Krolick KA. Wisnieski BJ. Sercarz, EE. Differential lateral mobility of IgM and Gig receptors in mouse B lymphocyte membranes. Proc. Natl. Acad. Sci. USA. (1977) 74(10): 4595-4599). Since the nature of the aptamer-epitope interaction is non-linear, the aforementioned changes in both aptamer and the membrane of the lymphocytic cells with temperature might negatively affect the complex, leading to dissociation.

Use of DNA aptamers as therapeutic carriers may be effective for several reasons. The small size of the aptamers is expected to yield desirable pharmacokinetic properties, allowing higher signal to background ratio from more rapid penetration to extra-vasculature tumor sites, as well as more rapid clearance. The molecular weights of the aptamers described are 52 kDa for the tetravalent aptamer and 39 kDa for the trivalent aptamer, which is below the estimated molecular weight cutoff for kidney clearance. Rapid clearance may be critical to keeping toxicity low when using these aptamers as radiologic or chemotherapeutic drug delivery agents.

An important step in increasing the selectivity of current therapeutic approaches is the development of novel molecular constructs that target specific epitopes expressed in diseased cells. The B cell receptor, which is the cell membrane Ig and the hallmark of the B cell, is an attractive target for therapeutic regulation of normal and euplastic B cell function. In addition, the BCR may also serve as a target for directed cytotoxicity, for example via a ligand or an antibody for example. However, there are no approved antibody agents that target the BCR, mainly due to interference by the large quantities of circulating forms of secreted Ig in the plasma. As noted above, the optimized aptamers herein do not bind to the soluble target molecule.

So far, there are no reports of a molecule that targets the mIgM in BCR, at physiological temperatures. The development of a locked nucleic acid (LNA) stabilized multimeric DNA aptamer that specifically binds to the membrane IgM (BCR) on neoplastic B cells, is merely one example of the teachings embodied herein applied to a particular target molecule, and can be readily carried out on other aptamers or guide the creation of aptamers that will find significant therapeutic or diagnostic utility. Rational chemical engineering was used to design the multimeric versions and are applicable to other aptamers targeting other molecules, including: 1) the linear assembly of the monomeric version using PEG linkers. Linear assembly allowed the use of automated synthesis, eliminating the bio-conjugation procedures typically used in developing multivalent constructs. 2) Systematic truncation of the aptamer coupled with 3) modification with LNA to increase conformational stability and nuclease resistance. 4) Trimeric and tetrameric versions with 5) optimized polyethylene glycol (PEG) linker lengths to yield high avidity at physiological temperatures both in vitro and in vivo.

Pharmaceutical Compositions and Methods of Treatment

The treatments embodied herein by optimized aptamer compounds and pharmaceutical compositions can be, in another embodiment, administered to a subject by any method known to a person skilled in the art, such as parenterally, paracancerally, transmucosally, transdermally, intramuscularly, intravenously, intradermally, subcutaneously, intraperitoneally, intra-ventricularly, intracranially, intravaginally or intratumorally. Utilizing certain delivery systems, the aptamers embodied herein can be delivered orally.

The term "subject" refers in one embodiment to a mammal including a human in need of therapy for, or susceptible to, a condition or its sequelae. The subject may include dogs, cats, pigs, cows, sheep, goats, horses, rats, and mice and humans. Other domesticated and livestock animals are also embraced by the embodiments herein. The term "subject" does not exclude an individual that is normal in all respects.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

Other conjugates embodied herein include conjugates of aptamers to scaffolds, sugars, proteins, antibodies, polymers, and nanoparticles, by way of non-limiting examples.

The compositions also include, in another embodiment, incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers, as described above, such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active and the inert carrier or diluent, a hard gelatin capsule.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic or diagnostic agents. In another embodiment, these agents are appropriate for the disease or disorder that is being treated, as is well known in the art. In particular, if the improved aptamer is used to deliver a payload such as a cytotoxic agent, siRNA, or even a radionuclide for imaging or therapeutic purposes, conjugates or combinations of the improved aptamer described herein and the additional therapeutic or diagnostic agent are fully embraced herein, and aptamer compositions having a certain sequence or consisting of a certain sequence are further understood to comprise such an additional agent or agents.

The dosage amount and frequency will be dictated, in one embodiment, by the desired therapeutic effect of the compound and its bioavailability by the route of administration. The appropriate dose and frequency can be determined readily by the skilled artisan in animal models and clinical testing.

The following examples are presented in order to more fully illustrate the preferred embodiments of the invention. They should in no way be construed, however, as limiting the broad scope of the invention.

EXAMPLES

Materials and Methods. Cell lines, Ramos (Burkitt's lymphoma), Daudi (Burkitt's lymphoma), Raji (Burkitt's lymphoma), Jeko (Mantle cell lymphoma), SKLY-16 (B cell lymphoma), CRW22R (Prostate cancer), H5V (Endothelial cells), HCT116 (Colorectal carcinoma), HEK293 (Human embryonic kidney), HeLa (Human adenocarcinoma cervical), K562 (Leukemia chronic myelogenous), MOLT (acute lymphoblastic Leukemia), SKOV-3 (Human adenocarcinoma ovarian), HL60 (acute myelocytic leukemia), Jurkat (T lymphocyte), SKLY-18 (B cell lymphoma) were purchased from ATCC except for SKLY16 and 18. All of the cells were cultured in RPMI 1640 medium supplemented with 100 units/ml penicillin-streptomycin and 10% fetal bovine serum (heat-inactivated; Invitrogen). Clinical samples were obtained from patients at Memorial Sloan Kettering Cancer Center or from healthy donors, on IRB approved protocols.

Phosphoramidites: spacer phosphoramidite 18 (sp18), amino modifier C6-dT, 5'-fluorescein phosphoramidite, Cy3™ phosphoramidite, and all the DNA reagents that are needed for DNA synthesis were purchased from Glen Research. Locked nucleic acids dT and dC, were purchased from Exiqon, TetVA.8S, L-TetVA.8S were purchased from Trilink Biotechnologies Inc.

All the DNA oligo sequences were chemically synthesized attaching a fluorophore at the 5' end using standard solid phase phosphoramidite chemistry on an ABI394 DNA synthesizer using either a 0.2 µmole or 1 µmole scale. The completed DNA sequences were de-protected. The crude product was purified using HPLC (Beckman Coulter System Gold Bioessential 125/168 diode-array detection instrument) equipped with a C-18 column (Dyanamax 250×10 mm, Varian) using 0.1M TEAA as the mobile phase. The length of each DNA construct was confirmed using 10%-TBE urea polyacrylamide gel electrophoresis. Full length DNA was quantified by measuring the absorbance at 260 nm and absorbance of the corresponding dye at the 5' position using a Cary Bio-100 UV-Visible spectrophotometer (Varian). Sequences used in NMR experiments were further dialyzed overnight with 0.5 mM $NaHPO_4$ buffer using a MWCO 1000 Da dialysis bag.

All the in vitro experiments were done using a binding buffer composed of RPMI 1640 and 4.5 g/L glucose (Sigma-Aldrich) and 5 mM $MgCl_2$ for monomers, 20 mM $MgCl_2$ for multimers (Sigma-Aldrich), 100 mg/L tRNA (Sigma-Aldrich), 100 mg/L single stranded DNA (Sigma-Aldrich), 100 mg/L BSA (Sigma-Aldrich) and binding was analyzed for binding using flow cytometry in binding buffer (Acurri C6) using binding buffer. We used 20 mM $Mg^{+2}$ for optimal for the folding of the aptamer in vitro and 5 mM $Mg^{+2}$ for experiments in vivo. The binding buffer consists of tRNA and single stranded DNA that are capable of scavenging $Mg^{+2}$ thereby reducing the effective concentration of Mg ions. The concentrations of $MgCl_2$ used did not show any toxicity towards the cells. Wash buffer was composed of RPMI1640 with 20 mM $MgCl_2$, 0.5%BSA.

Cell Binding Assays. Affinity of each construct was evaluated by incubating Ramos cells (2.5 ×$10^5$) with a series of FITC or Cy3 labeled constructs in a 50 µL of binding buffer on ice for 45 min Cells were then washed with 1 mL of wash buffer at 4° C. and resuspended in 100 µL of wash buffer. The binding of the constructs was analyzed using flow cytometry by counting 10,000 events for each concentration. As a positive control, a similar assay was performed using a FITC labeled anti-IgM antibody (1 µg, Goat anti human, Invitrogen) along with an isotype control (1 µg, Goat anti mouse IgG2a, Invitrogen). Binding at respective concentrations and absolute fluorescence intensity difference was used for the binding curves. When calculating the relative binding constant, binding curves were fitted with median fluorescence intensity observed for each histogram and observed Bmax/2 was used as the binding constant. Control random sequences with each fluorophore were synthesized separately and used to compare non-specific background binding. Assays were done using flow cytometry in which each data point reported corresponds to the median of 10,000 counted events. Investigation of the multimeric aptamer binding with clinical CLL and PBMC samples were done by incubating FITC-labeled multimeric aptamer (0.5 µM) or FITC labeled random control along with APC labeled anti-CD19 (0.5 µg), Cy5.5 labeled anti-CD45 (50 ng) with 1×$10^6$ cells (cultured or CLL) on ice.

After 45 min, the cells were washed with wash buffer and analyzed for binding using flow cytometry. Investigation of aptamer interaction of mIgM was done in 20, 50 or 100% human serum supplemented with 20 mM $MgCl_2$ for multimeric aptamers, 5 mM $MgCl_2$ for monomeric aptamers using similar protocol as above.

Nuclease Stability. Aliquots of 50 pmole of multivalent constructs the labeled with a fluorophore were incubated at 37° C. in a final volume of 20 μL in human serum and in 20uL of PBS buffer for 0, 0.5 1, 2, 4, 6, 8, 10, 24, hours. At the end of each time point, the reactions were terminated by adding 20 μL 2× nucleic acid loading buffer (Bio-Rad) and stored in −80° C. Full length and digested DNA were analyzed by 10%-TBE urea polyacrylamide gel electrophoresis and fluorescence was quantified using FUJI FILM multi gauge V2.2 software. The average half-lives were calculated with Prism V fitting to exponential decay.

Trypsin Digestion Experiments. Cold PBS washed $5×10^5$ Ramos cells were incubated with 1 mg/mL trypsin (TPCK treated, Sigma T1426) in 500 μL of 0.05% Trypsin EDTA 1X in HBSS (Cellgro 25-052-C1) for 40 min at 37° C. The incubation time was optimized by initial pilot experiments with varying incubation times from 10-40 min. The trypsin cleavage site is masked; therefore longer incubation times were needed to observe optimal cleavage. In earlier time points, we did not observe significant reduction in binding with cells both by the aptamer or anti-IgM antibody. After incubation, cells were pelleted, washed with cold PBS, and aliquots were incubated with 1 μM of TD05.1, 1 μM of Random DNA, anti-CD20 and FITC labeled goat anti-human IgM antibody (1 μg) along with an isotype control (1 μg, Goat anti mouse IgG2a, Invitrogen) for 45 min at 4° C. Then the cells were washed and resuspended in cold PBS containing 20 mM $MgCl_2$ and 0.5% BSA, and the binding was detected using flow cytometry (Becton Dickinson FacsCalibur 2002 model).

In Vivo Binding Assay. Female athymic nude mice, 4-8 weeks of age (Taconic, Germantown, N.Y.) were inoculated i.p. with $7×10^6$ Ramos cells in 0.5 mL of saline. After 10 minutes, 0.5 mL of a 1 μM solution of TetVA.8S or random aptamer in saline was introduced i.p. Animals were sacrificed after 1 hour and the intraperitoneal cavity was flushed by 10 mL PBS and collected the cells. The cells were divided into 3 aliquots and incubated with binding buffer supplemented with (1) 0.5% BSA, (2) 10 μg/mL of anti-CD19, (3) 200 μg/mL of anti-IgM antibody for 30 minutes in ice. The cells were then washed using 1mL of washing buffer and binding of the aptamer and the antibody was investigated using flow cytometry counting 10,000 events (Becton Dickinson FacsCalibur 2002 model). Prior to the experiment, animals were housed in filter-top cages and provided with sterile food, water, and bedding. Animal protocols were approved by the Animal Care and Use Committee at Memorial Sloan-Kettering Cancer Center.

In certain discussions herein, the theory by which a product operates may be described. Applicants are not required to disclose the reason or theoretical basis why a product or process operates in a certain manner, and are not bound by said disclosure.

Example 1

Modification of TD05

Figure 8:
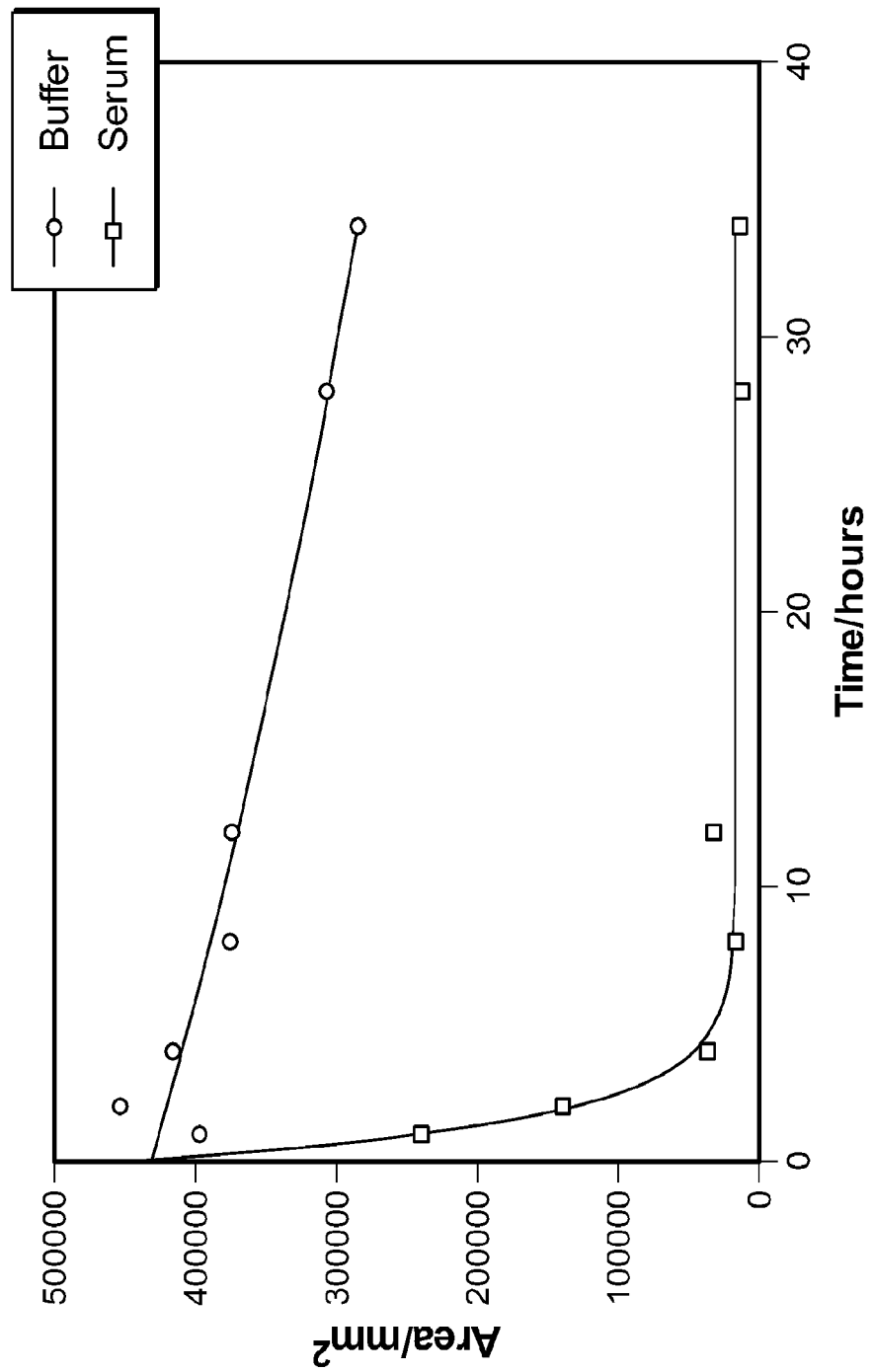
FIG. 8 is an analysis of nuclease stability of TD05 in serum at physiological temperature using polyacrylamide gel electrophoresis. Fluorescence intensity of full length DNA /area ($mm^2$) was plotted as a function of time (hours).
Figure 9:
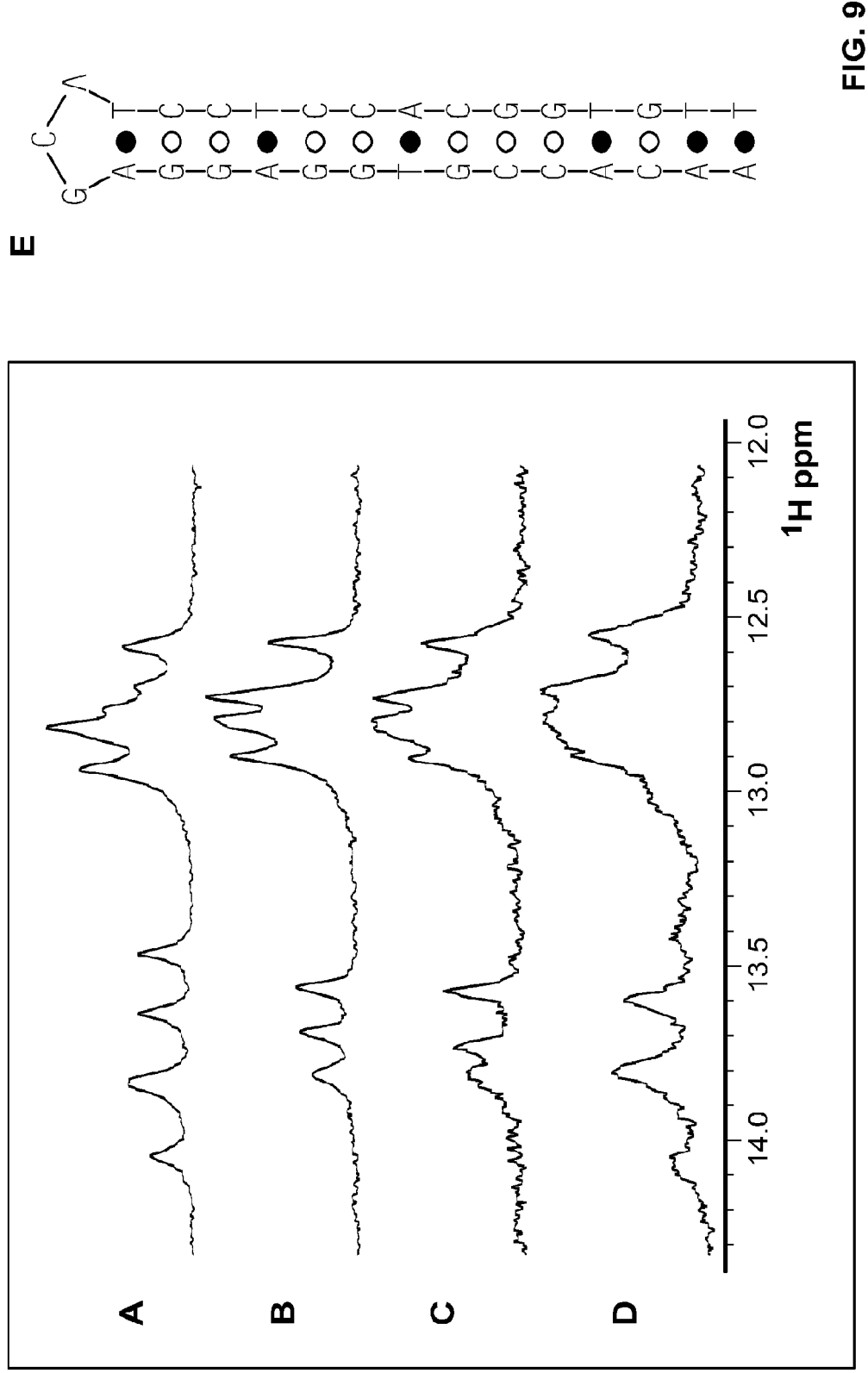
FIG. 9 shows the NMR characterization of stem-loop formation. 1D NMR spectra of DNA samples were recorded on 600 MHz Varian Unity-Inova spectrometers with jump-and-return water suppression (512-1024 transients), in 0.5 mM $NaHPO^4$ containing 4mM NaCl with 10% of $D_2O$ at temperatures indicated below. (A) NMR spectrum recorded at 37° C. for the structure in panel E, which is the palindromic region of TD05 used as the positive control to detect the formation of the stem structure in NMR experiments. Five peaks at 13.5-14 ppm (one doubled) for internal AT pairs, and eight GC pairs appear between 12.5-13.0 ppm. (B) NMR spectrum of structure A (in FIG. 1) at 37° C., with three internal AT base pairs and seven GC pairs suggesting that predominant stem formation leads to a more homogeneous structure at 37° C. (C) and (D) NMR spectra of the oligonucleotide A (in FIG. 1) recorded at 25° C. and 0° C., indicating contribution of other folds to populations of the molecules at lower temperatures (line broadening and less resolved peaks).

Truncation. TD05 was unstable at physiological conditions and unable to bind its target on Ramos B cell lymphoma (FIGS. 7 and 8). The predicted secondary structure of the TD05 using m-fold was a 'hairpin' structure (FIGS. 1 and 7, m-fold is a software application used to predict secondary structure of DNA; Zuker M. Mfold web server for nucleic acid folding and hybridization prediction. Nucleic Acids Res. (2003) 13: 3406-3415). Structural studies of a stem identical to the palindromic region of TD05 and full length TD05 (FIG. 9) using NMR showed predominant formation of the stem at 37° C. Broadening of the peaks with decreasing temperature suggested the loss of homogeneity of the secondary structure. At lower temperatures therefore, TD05 might be forming multiple folds that lead to a more heterogeneous mixture, with only a few structures that fit the target epitope.

FIG. 1 shows the optimization of monomeric and multimeric scaffolds and their Bmax/2 (Kd') at 37° C. (top number) and at 4° C. (bottom number). A. original TD05 sequence, B. Truncated TD05.1, C. LNA modified TD05.1 (TD05.17), D. Bivalent TD05.17 (L-BVA.8S), E. Trivalent TD05.17 (L-TVA.8S), F. Tetravalent TD05.17 (L-TetVA.8S). The constructs were synthesized with PEG at the 5' and 3' ends; Cy3 or FITC was added at the 5' end. Circled nucleotides indicate LNA bases.

The original TD05 aptamer consisted of 48 nucleotides and a later truncated version of 44 nucleotides was reported by removing bases from the ends (Tang et al. 2007, op. cit; Mallikaratchy P, Tang Z, Meng L, Shangguan D, Kwame S, Tan W. Aptamer directly evolved from live cells recognizes membrane bound immunoglobin heavy mu chain in Burkitt's lymphoma cells. Mol. Cell. Proteomics (2007) 6: 2230-2238; Mallikaratchy P, Tang Z, Tan W. Cell Specific Aptamer Photosensitizer Conjugates as a Molecular Tool in Photodynamic Therapy. Chem Med Chem. (2008) 3(3): 425-427). Because affinity was retained in the truncated version, in which the stem was shortened, it is likely that bases in the central loop region of the aptamer play the most important role in binding. The possibility of further truncating TD05 was investigated with the aim of increasing the affinity by stabilizing the secondary structure of TD05. Bases were truncated starting from the 3' and 5' region (FIG. 1). Shorter versions, e.g. TD05.1, showed higher affinity than the original version even after 10 nucleotides were removed (Table 1). The reduction of the length of the TD05 stem could be leading to a population with more stable secondary structure containing a favorable fold that better fit the protein-binding site. In addition, shorter sequences could also be synthesized with higher yields and lower costs, which was particularly important for a strategy in which multimeric aptamers were planned.

TABLE 1

Modifications of TD05 alter binding at 4° C.

| name | Deletions/changes | Bmax/2 at 4° C. (nM) |
|---|---|---|
| TD05 | ACCGTGGAGGATAGTTCGGTGGCTGTTCAG GGTCTCCTCCACGGT (SEQ ID NO: 1) FIG. 1, structure A | 359 |
| TD05.7 | XXCGTGGAGGATAGTTCGGTGGCTTCAGGGTCTCC TCCCGXX (SEQ ID NO: 2) | 148 |
| TD05.1 | XXXXXAGGAG GATAGTTCGGTG GCTGTTCAG GGTCTCCTCCTXXXXX (SEQ ID NO: 3) FIG. 1, structure B | 53 |

TABLE 1-continued

Modifications of TD05 alter binding at 4° C.

| name | Deletions/changes | Bmax/2 at 4° C. (nM) |
|---|---|---|
| TD05.10 | GGAGGANAGTTCGGTGGCTGTTCAGGGTCTCCTCC (SEQ ID NO: 4) | >1000 |
| TD05.11 | GGAGGATAGTTCGGTNGCTGTTCAGGGTCTCCTCC (SEQ ID NO: 5) | >1000 |
| TD05.12 | GGAGGATAGTTCGGTGGCTGTNCAGGGTCTCCTCC (SEQ ID NO: 6) | >1000 |
| TD05.16 | +A + *G* + *G* +A GGATAGTTCGGTGGCTGTTCAGGGTCTCC + *T* + *C* + *C* + *T* (SEQ ID NO: 7) | 368 |
| TD05.17 | AGGAGGATAGTTCGGTGGCTGTTCAGGGTCTCC + *T* + *C* + *C* + *T* (SEQ ID NO: 8) FIG. 1, structure C | 43 |
| TD05.18 | +A + *G* + *G* +A GGATAGTTCGGTGGCTGTTCAGGGTCTCCTCCT (SEQ ID NO: 9) | 819 |

+N = LNA; italic, bold N = 2'OMe substituted nucleotides. X = deletions

LNA Incorporation. The incorporation of LNA bases to a stem region of a stem-loop structure has been shown to increase the melting temperature, nuclease stability, and overall stability of the secondary structure of aptamers (Hicke B J, Marion C, Chang Y F, Gould T, Lynott C K, Parma D, Schmidt P G, Warren S. Tenascin-C aptamers are generated using tumor cells and purified protein. J. Biol. Chem. (2001) 276 (52): 48644-48654; Schmidt K S, Borkowski S, Kurreck J, Stephens A W, Bald R, Hecht M, Friebe M, Dinkelborg L, Erdmann V A. Application of locked nucleic acids to improve aptamer in vivo stability and targeting function. Nucleic Acids Res. (2004) 32(19): 5757-5765; Shangguan D, Tang Z, Mallikaratchy P, Xiao Z, Tan W. Optimization and modifications of aptamers selected from live cancer cell lines. Chembiochem. (2007) 8(6): 603-606). This is mainly because LNA modified oligonucleotides, derived from the constrained sugar moiety with 3'-endo conformation resulting from the methylene link between the 2' oxygen and 4' carbon of the ribose ring exhibit increased affinity towards their cDNA (Kaur H, Babu B R, Maiti S. Perspectives on chemistry and therapeutic applications of locked nuleic acid (LNA). Chem. Rev. (2007) 107: 4672-4697). The further stabilization of the stem by inclusion of LNA was postulated to also increase the in vivo stability of the secondary and tertiary structures. LNA was incorporated into the stem region of TD05.1 in three different combinations by substituting purines and pyrimidines (TD05.16), pyrimidines only (TD05.17), and purines only (TD05.18) (Table 1). The low binding of TD05.18 suggests LNA substitution of purines A 1 G2G3A4 had a profound effect on the secondary and tertiary structure (Table 1). Substitution of the pyrimidines T32C33C34T35 with LNA further increased the dissociation constant, indicating that these bases may not be involved in binding, but may aid in stabilizing the stem region. Attempts to introduce nuclease resistant 2'-OMe bases into the loop region impaired binding, yielding a Bmax/2 values higher than the TD05.1, suggesting that the loop region cannot be modified with nuclease resistant 2'OMe (Table 1). Difficulties in introducing the modified bases within an aptamer sequence have been reported before, and the loss of binding is probably due to changes of the favorable fold of the aptamer (Schmidt K S, Borkowski S, Kurreck J, Stephens A W, Bald R, Hecht M, Friebe M, Dinkelborg L, Erdmann V A. Application of locked nucleic acids to improve aptamer in vivo stability and targeting function. Nucleic Acids Res. (2004) 32(19): 5757-5765).

Multivalent TD05.1 Constructs and Optimization of the Linker Lengths. One strategy to decrease the dissociation rates is to increase local concentration by multimerization of the ligand. The resulting decreased dissociation rates might also be useful in vivo. In therapeutic applications, lower retention times would likely decrease the therapeutic index. Therefore, based on the improved affinity and stability of TD05.1, multivalent analogs were designed with PEG linkers in an attempt to increase affinity at physiological temperatures (FIG. 1).

While several approaches to multivalent designs are possible, linear molecular assembly of TD05.1 using poly-ethylene-glycol (PEG) linkers were pursued, because this would also more likely allow cross-linking of BCR on the cell surface, which might in turn lead to internalization of the complex for delivery of cytotoxic cargo or to modulation of BCR signal transduction pathways. However, the embodiments are not limited only to linear molecular assemblies or polyethylene glycol. PEG phosphoramidite is commercially available for solid state synthesis of multivalent analogs, so this linker was chosen to construct various linear multivalent aptamer forms. Linker length between aptamer binding sites was optimized to avoid steric hindrance and to promote binding. Most naturally occurring antibodies are bivalent; therefore, first, a bivalent (BV) TD05.1 was designed. In order to mimic dimensions of an antibody and provide appropriate spatial flexibility to promote binding of a bivalent aptamer, linker lengths of 6 [(sp18)$_6$], 8 [(sp18)$_8$] and 12 [(sp18)$_{12}$] (lengths correspond to 12.6 nm, 16.8 nm, and 25.2 nm) were designed and their binding to Ramos cells was evaluated using flow cytometery. The PEG spacer (sp18) was approximately 2.1 nm in length, which has been reported elsewhere (Kim Y, Cao Z, Tan W. Molecular assembly for high-performance bivalent nucleic acid inhibitor. Proc. Natl. Acad. Sci. U S A. (2008) 105(15): 5664-5669) and this approximation was assumed for this study. Observed binding for bivalent analogues was similar to monomeric TD05.1 at 37° C.; however, at 4° C. BV.8S showed slightly higher binding than BV.6S and BV.12S indicating that bivalent design with 8 linkers, which corresponds to 16.8 nm, is more favorable for the bivalent design. Therefore, the linker length of 16.8 nm on the bivalent version of TD05.17 (i.e. L-BVA.8S) was evaluated, assuming that increased structural stability of the stem along with the dimerization might play additive roles in increasing avidity. L-BVA.8S did show a significant increase in the Bmax/2 at 37° C. (Table 2). However, this increment was likely still inadequate for in vivo applications. This suggested that increasing valency by two, alone, was not enough to substantially increase avidity. Subsequently, eight sp18 linkers were used to design trivalent (TVA.8S) and tetravalent (TetVA.8S) TD05.1-based aptamers to further investigate the binding avidity (FIG. 1).

The aforementioned linker length optimization process can readily carried out for other aptamers by the skilled artisan.

Figure 2:
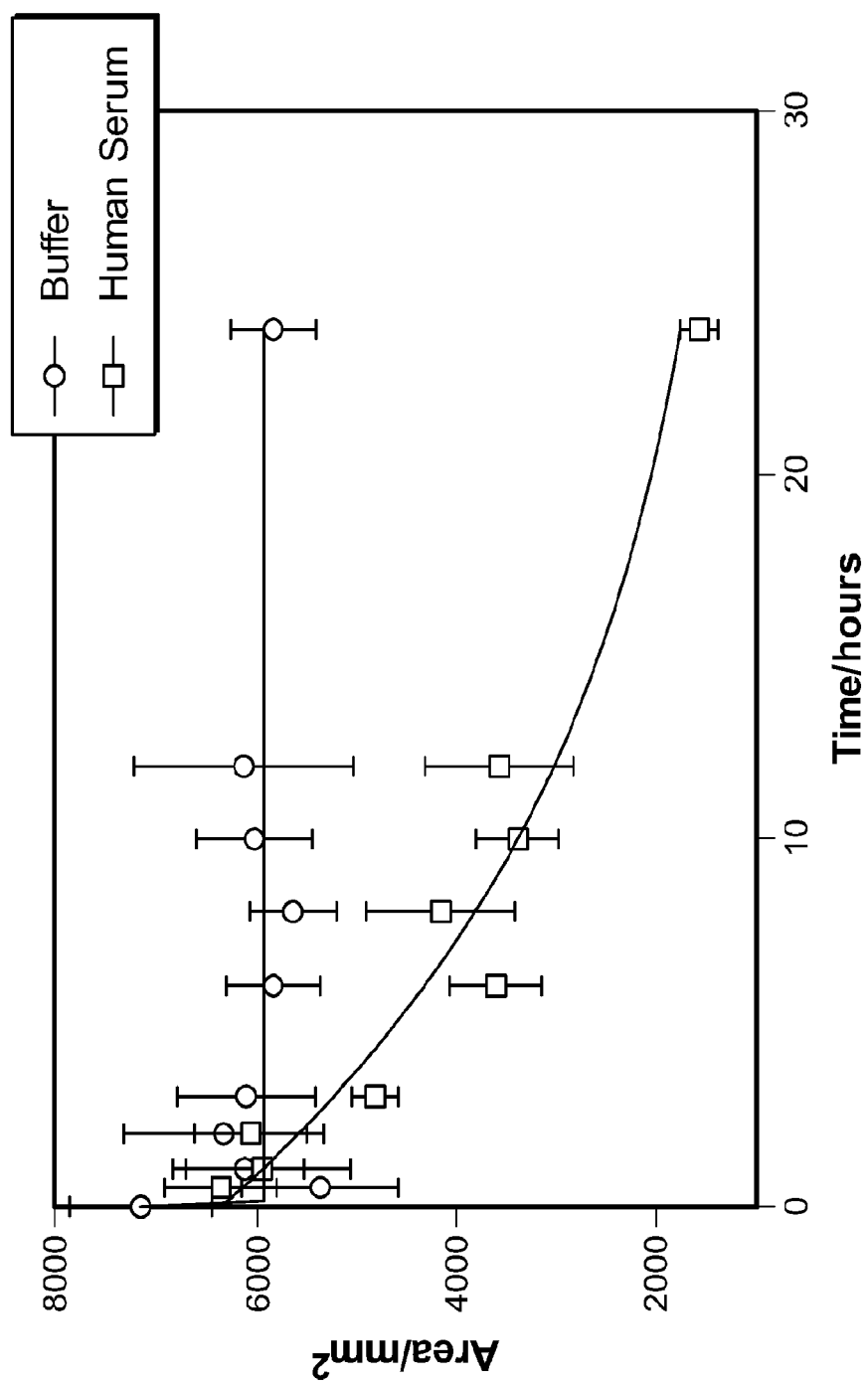
FIG. 2 shows the analysis of nuclease stability of L-TVA.8S in human serum at physiological temperature. Aptamers were separated using poly-acrylamide gel electrophoresis and fluorescence intensity of full length DNA/area (mm$^2$) was plotted as a function of time (hours).
Figure 10:
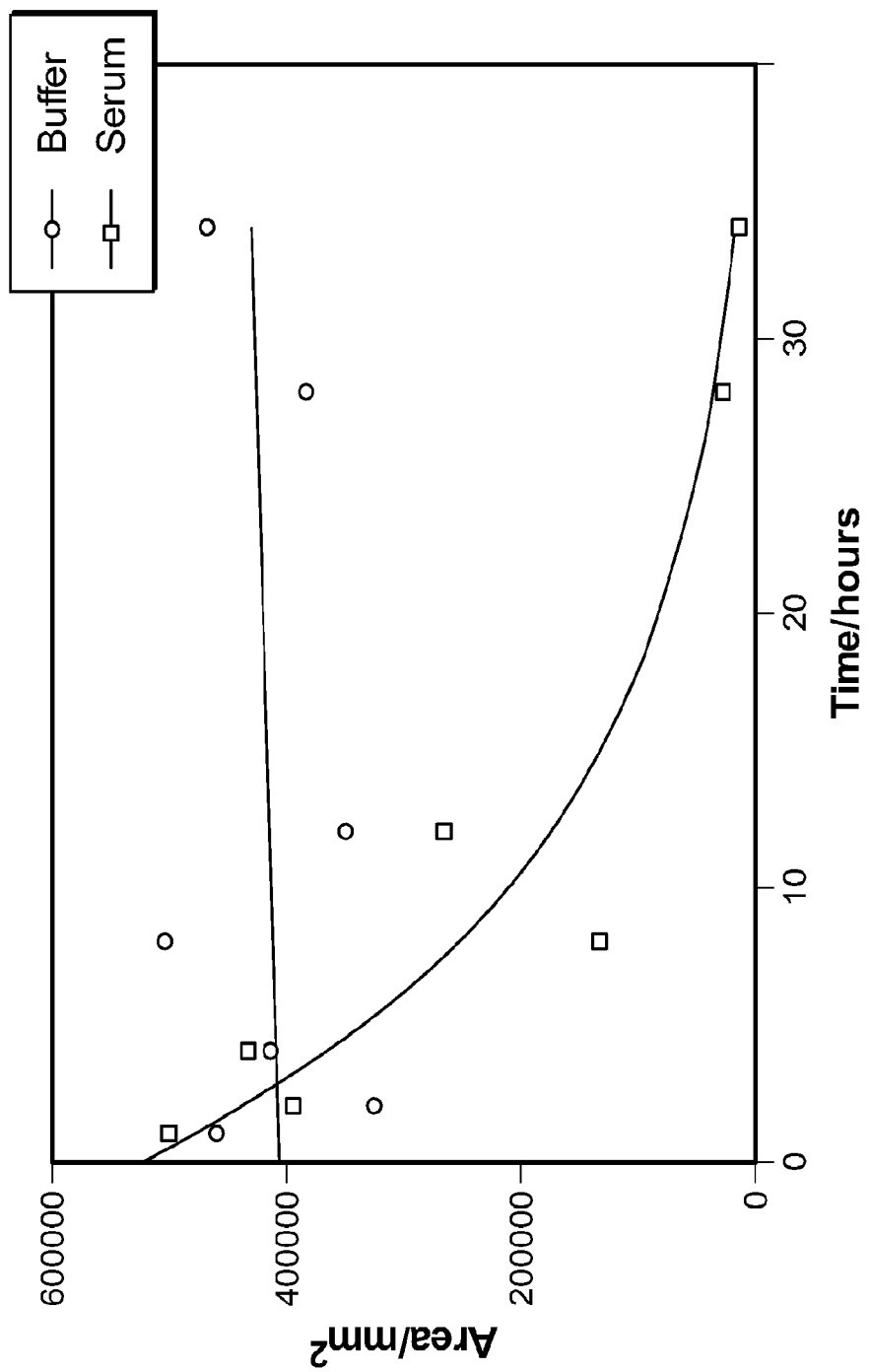
FIG. 10 is an analysis of nuclease stability of L-BVA.8S in serum at physiological temperature using poly-acrylamide gel electrophoresis. Fluorescence intensity of full length DNA /area ($mm^2$) was plotted as a function of time (hours).
Figure 11B:
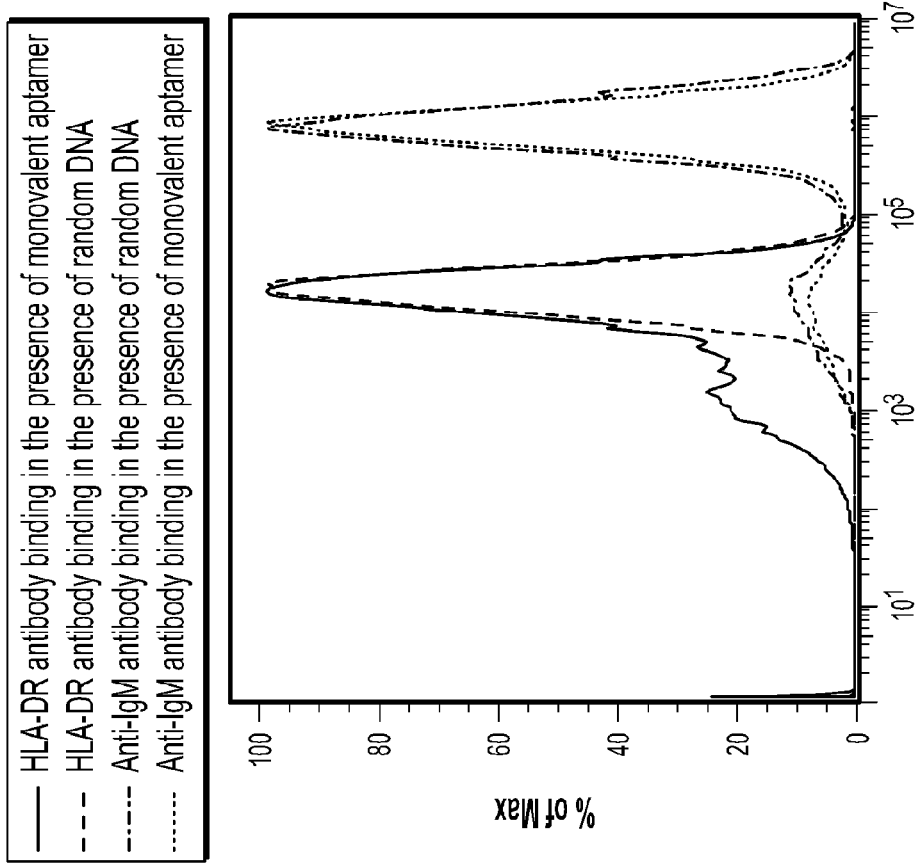
FIG. 11 shows the competition of anti-IgM antibody with monomeric (A-B) and tetrameric aptamer (C-D). In order to investigate the competition between anti-IgM (mu) antibody and tetrameric aptamer, first 0.2 ug/mL of cy5-labeled anti-IgM (mu) antibody and isotype control were incubated with $1\times10^6$ Ramos cells in ice for 30 min Then the free antibody was washed with lmL of wash buffer, and cells were reconstituted with either 0.5 uM of FITC labeled monomeric or 0.25 uM tetrameric aptamer, or 0.5 uM or 0.25 uM of random control in 50 uL of binding buffer for another 30 min in ice. Then the cells were washed with lmL wash buffer and binding events were monitored in FL1 for the aptamer and FL4 for the antibody counting 10000 events using flowcytometry. Fluorescence intensity on the X axis for FL1 shifts to a lower value in the presence of anti-IgM antibody indicating that the anti-IgM replaces the aptamer.
Figure 11A:
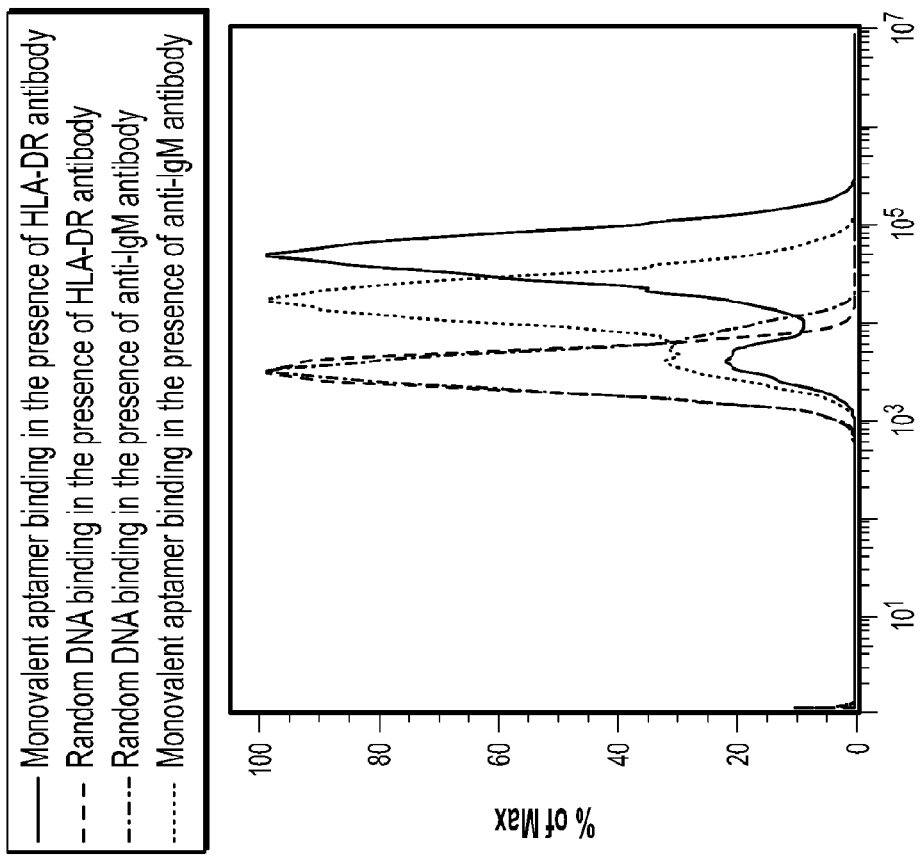
Figure 11D:
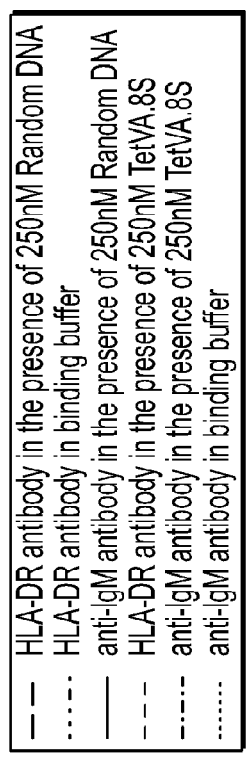
Figure 11D:
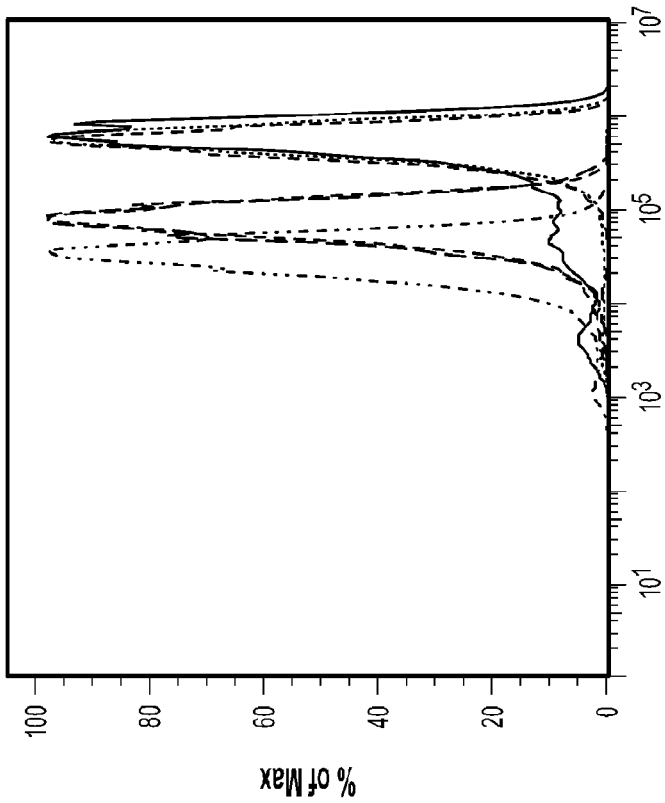
Figure 11C:
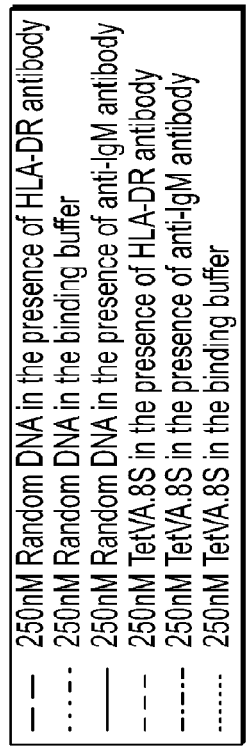
Figure 11C:
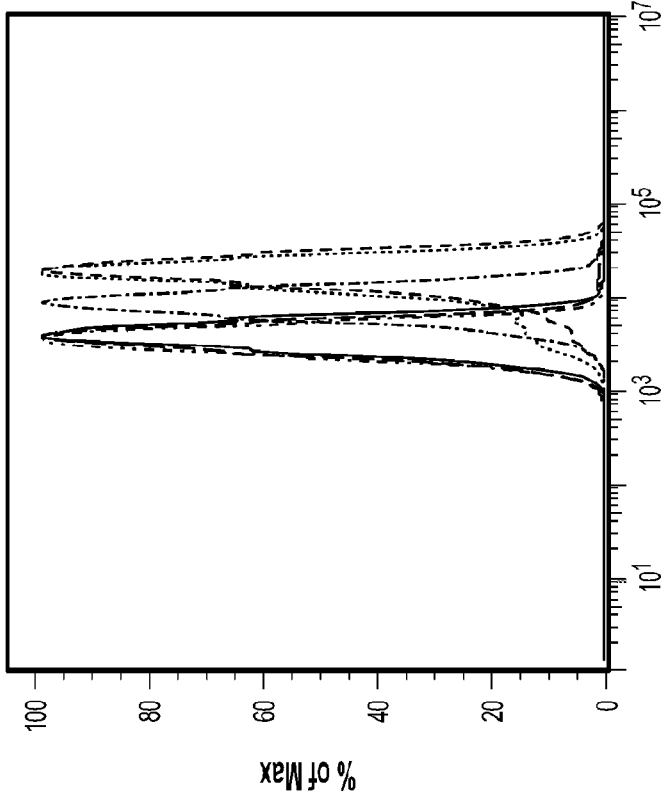

At 37° C., a trivalent aptamer (TVA.8S) using eight sp18 linkers between each monomeric aptamer, showed increased binding (Table 2). In order to determine whether the improved TVA.8S binding is a result of interaction of each of the three aptamers with epitopes vs. an improvement based on either length or geometry, a hetero-trimeric analogue of the homotrimeric TD05.1 was designed, in which the loop of the central monomer was randomized and linked to distal monomers using 8 PEG units (TVSR). At 4° C., the binding of the heterogenic TVSR was 3-4 times lower than that of the TVA.8S at a fixed concentration, suggesting that the internal monomer in the trivalent aptamer plays a role in increasing the avidity of the trimeric molecular assembly, either by altering structure or by adding an additional binding site. The decrease in the binding of TVSR also might be due to intramolecular interactions of the randomized region with the distal aptamers. Dimers with 16 and 20 linkers were designed to generate a dimeric version with a length similar to the TVA.8S. Binding at 4° C. of the long dimer BVA.20S was less than the TVA.8S suggesting that the longer linkers may be leading to unfavorable conformations. Alternatively, the longer length between the two monomers could make the dimer spatially unsuitable for binding. BVA.16S showed a Bmax/2 of 2030 nM at 37° C.; however, affinity of the dimer was not as high as the corresponding trivalent design. In addition, the tetravalent analog of TD05.1 showed no significant increment in binding. This might be due to the density of receptors on the cell surface limiting the increase in the dissociation constant. Alternatively, the binding interaction might be linker independent beyond 16.8 nm (containing LNA) as the monomer. The affinity of each construct was increased approximately 2-fold suggesting that the locked version of the aptamer aided in stabilizing the conformation of the stem (Table 2). The LNA modified multimeric versions were further modified with PEG spacers at the 3' and 5' ends to avoid 3' and 5'exonuclease activity. The original unmodified TD05 showed a half life of less than 1 h whereas L-TVA.8S showed an estimated half life of 8.75 h, demonstrating that the modifications introduced for TVA.8S significantly enhanced the nuclease stability in serum (FIG. 2). L-BVA.8S showed a half life of 7.87 h suggesting that multimerization and PEGylation contributes to increase stability (FIG. 10).

FIG. 2 shows an analysis of nuclease stability of L-TVA.8S in human serum at physiological temperature. Aptamers were separated using poly-acrylamide gel electrophoresis and fluorescence intensity of full length DNA/area (mm$^2$) was plotted as a function of time (hours).

Cell Specificity. The specificity of the divalent scaffold for B cells and B cell lymphoma, was investigated using fresh mononuclear cells from healthy donors, patients with chronic lymphocytic leukemia, cultured B-cell lymphoma cells expressing or not expressing mIgM, and cultured non-B cell cancers, using FITC labeled L-BVA.8S and quantified using

TABLE 2

Optimization of linker length and linear assembly of TD05.1

| Name | Sequence | Bmax/2@ 37° C. (nM) |
|---|---|---|
| TD05.1 | AGGAG GATAGTTCGGTG GCTGTTCAG GGTCTCCTCCT (SEQ ID NO: 10) FIG. 1, structure B | >10000 |
| BV.6S | TD05.1-(sp18)$_6$-TD05.1 (SEQ ID NO: 11) | >10000 |
| BV.8S | TD05.1-(sp18)$_8$-TD05.1 (SEQ ID NO: 12) | >10000 |
| BV.12S | TD05.1-(sp18)$_{12}$-TD05.1 (SEQ ID NO: 13) | >10000 |
| BV.16S | TD05.1-(sp18)$_{16}$-TD05.1 (SEQ ID NO: 14) | 2030 |
| TVA.8S | TD05.1-(sp18)$_8$-TD05.1-(sp18)$_8$-TD05.1 (SEQ ID NO: 15) | 490 |
| TetVA.8S | TD05.1-(sp18)$_8$-TD05.1-(sp18)$_8$-TD05.1-(sp18)$_8$-TD05.1 (SEQ ID NO: 16) | 425 |
| TD05.17 | AGGAGGATAGTTCGGTGGCTGTTCAGGGTCTCC + *T* + *C* + *C* + *T* (SEQ ID NO: 17) FIG. 1, structure C | >10,000 |
| L-BVA.8S | FITC-sp18-TD05.17-(sp18)$_8$-TD05.17-sp18 (SEQ ID NO: 18) FIG. 1, structure D | 6222 |
| L-TVA.8S | Cy3-Sp18-TD05.17-(sp18)$_8$-TD05.17-(sp18)$_8$-TD05.17-Sp18 (SEQ ID NO: 19) FIG. 1, structure E | 256 |
| L-TetVA.8S | Cy3-sp18-TD05.17-(sp18)$_8$-TD05.17-(sp18)$_8$-TD05.17-(sp18)$_8$-TD05.17-sp18 (SEQ ID NO: 20) FIG. 1, structure F | 272 |

+*N* = LNA; Sp18 = spacer 18,

To further investigate the improved affinity, the tri- and tetra-valent scaffolds were re-synthesized using TD05.17 flow cytometry. An analogous randomized aptamer sequence linked with 8 PEG units was used as the isotype control. There was generally little non-specific binding to cells not expressing surface mIgM, whereas B cell lymphoma cell lines expressing mIgM and B cells gated from clinical samples were usually positive (Table 3).

TABLE 3

Analysis[a] of specificity of dimeric aptamers with cultured cells and clinical samples

| Cell Line | Cell Type | Bivalent aptamer |
|---|---|---|
| Ramos | B-Lymphoma, Burkitt's IgM+ | + |
| SKLY-16 | B-lymphoma IgM+ | + |
| Daudi[b] | B-lymphoma IgM+ | + |
| Raji | B-Lymphoma, Burkitt's IgM+ | − |
| Jeko | Mantle Cell Lymphoma (B) | − |
| Bjab | B-Lymphoid Leukemia | − |
| SKLY 18 | B-lymphoma IgM− | − |
| AL67 | Mouse fibroblast | − |
| CRW22R | Prostate cancer | − |
| H5V | Endothelial cell lines (heart) | − |
| HCT116 | Carcinoma Colon | − |
| HEK293 | Human embryonic kidney | − |
| HeLa | Human Adenocarcinoma (cervical) | − |
| K-562 | Leukemia, Chronic Myelogenous | − |
| MOLT | T-Leukemia, acute lymphoblastic | − |
| SKOV-3 | Ovarian | − |
| HL60 | Leukemia, acute promyelocytic | − |
| Jurkat | T-Leukemia, acute | − |
| CML[c] | Clinical sample | − |
| CLL[d] | Clinical Samples | + |
| HCL[e] | Clinical Sample | + |
| Normal B cells[f] | Donors | +/− |
| Normal T cells[g] | Donors | − |

[a]Median of the fluorescence intensity of FITC-labeled Aptamer/Median of the fluorescence intensity of FITC labeled Random sequence ≥2.0 equals positive (+). Experiments were done at 4°.
[b]Variable binding to Daudi was observed.
[c]One sample. CML is chronic myeloid leukemia, a non-B cell neoplasm.
[d]Fourteen samples; CLL is B-Chronic Lymphocytic Leukemia. In two of the samples, the gated CD19 negative population showed positive signal with the aptamer
[e]One sample. HCL is Hairy Cell Leukemia, a B cell neoplasm.
[f]Nine samples; Five of the normal B cell samples were negative and three were only weakly positive.
[g]Twenty three samples. A small subpopulation of one of the normal T cell samples was weakly positive.

Figure 3:
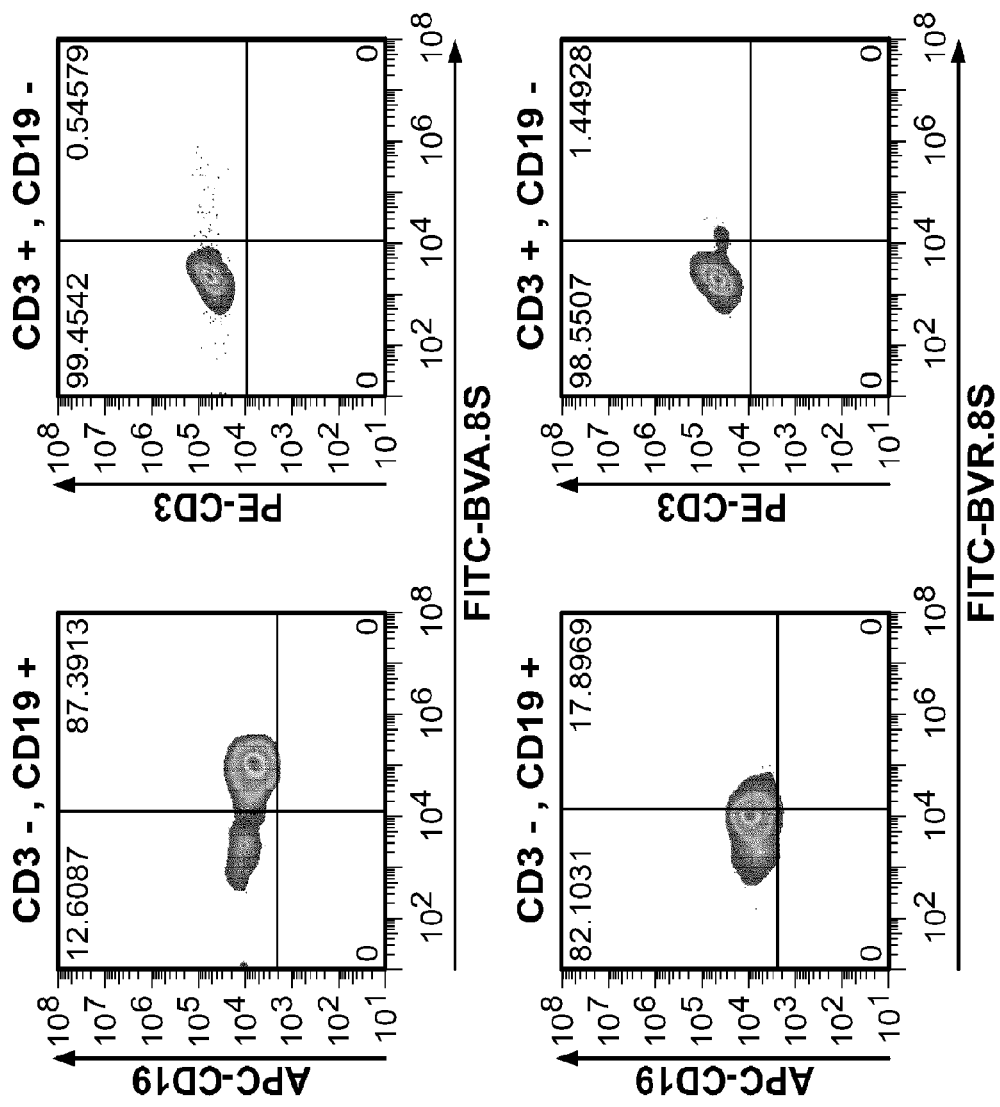
FIG. 3 shows the binding of LNA modified bivalent aptamer binding with B cells and T cells. Upper-left: Bivalent aptamer binding to CD19 positive B cells, Upper-right: Bivalent aptamer does not bind to CD3 positive, CD19 negative cells. Lower-left: Bivalent randomized control aptamer does not bind to CD19 positive cells, Lower-right: Bivalent randomized aptamer does not bind to CD3 positive cells.

Interestingly, B cells obtained from healthy individuals only sometimes stained positively for L-BVA.8S aptamer. CD3 positive T-cells rarely bound to this aptamer, further confirming the specificity (FIG. 3). However, several of the mIgM expressing B cell lymphoma cell lines and clinical samples did not bind the aptamers (Table 3), perhaps because the epitope was masked or the expression levels were low, suggesting that while specificity was high, sensitivity was lower (Table 3). In addition, the TVA.8S displayed poor binding to fresh samples as compared to the BVA.8S, although competition analyses demonstrated that both bivalent and trivalent aptamers competed for binding of the monomeric aptamer to Ramos. These data suggest that subtle differences in the local environment of the epitope may be affecting the ability of the different sized aptamers to bind to fresh samples.

FIG. 3 shows binding of LNA modified bivalent aptamer binding with B cells and T cells. Upper-left: Bivalent aptamer binding to CD19 positive B cells, Upper-right: Bivalent aptamer does not bind to CD3 positive, CD19 negative cells. Lower-left: Bivalent randomized control aptamer does not bind to CD19 positive cells, Lower-right: Bivalent randomized aptamer does not bind to CD3 positive cells.

Figure 4:
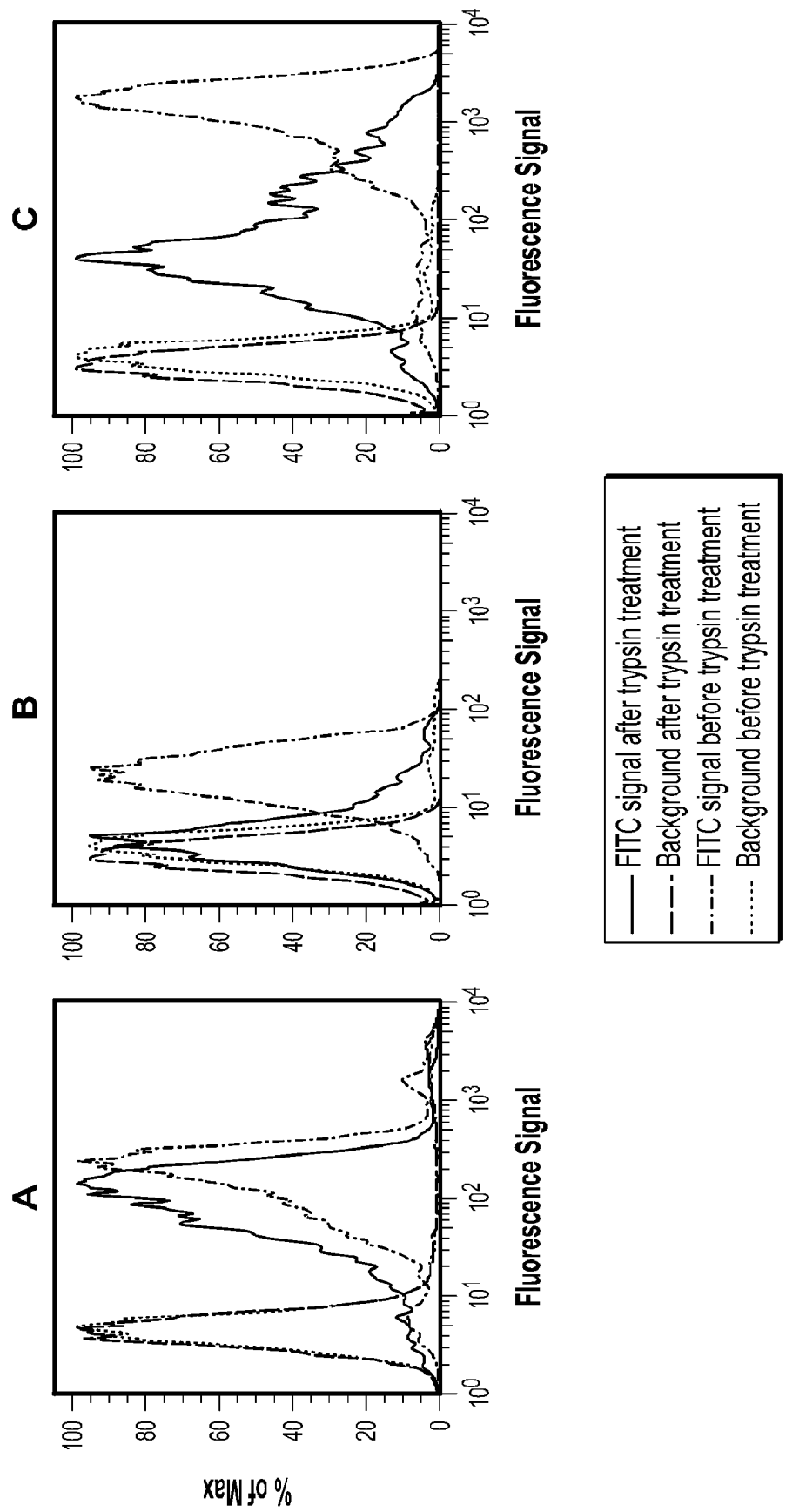
FIG. 4 shows the binding of TD05.1 to mIgM after trypsin treatment. Cells were treated with trypsin for 40 min and binding of FITC labeled (A) TD05.1, (B) anti-CD20, and (C) anti-IgM antibody, was evaluated and compared with untreated control.

As previously reported, the monomeric aptamer TD05 competed with the anti-IGHM (anti-Immunoglobin Heavy Mu Chain) antibody for binding to Ramos cells indicating that the aptamer binding site was located on or near the IgM heavy chain (Mallikaratchy P, Tang Z, Meng L, Shangguan D, Kwame S, Tan W. Aptamer directly evolved from live cells recognizes membrane bound immunoglobin heavy mu chain in Burkitt's lymphoma cells. Mol. Cell. Proteomics (2007) 6: 2230-2238). We determined whether the multimeric aptamer could retain binding in the presence of the anti-IGHM antibody. In the presence of anti-IgM antibody, fluorescence shifts to the background level for the multimeric aptamer scaffolds, which demonstrated that anti-IgM competes with the aptamer (FIG. 11). This suggests that multimerization does not change the specificity. These data in sum lead to the conclusion that the multimeric aptamer interaction is selective for an epitope on the mIgM itself Aptamers Recognize Membrane Bound mIgM, But Not Soluble IgM. Soluble Ig is found in high concentrations in plasma. Hence, one of the major drawbacks in using anti-Ig antibodies as therapeutic vehicles for the treatment of lymphoma is that these antibodies interact with the soluble Ig in serum leading to immune complexes that are cleared. Thus, binding is significantly limited at tumor targets. mIgM contains an additional 41 amino acids that are not present in the soluble IgM, which are present in or near the membrane. Approximately 15 of these amino acids are found extracellularly (Cambier, J C, Campbell K S. Membrane immunoglobin and its accomplices: new lessons from an old receptor. The FASEB Journal. (1992) 6: 3207-3217; Rogers J, Early P, Carter C, Calame K, Bond M, Hood L, Wall R. Two mRNAs with different 3 ends encode membrane-bound and secreted forms of immunoglobulin chain. Cell. (1980) 20(2): 303-312; Friedlander, R. M., Nussenzweig, M. C., Leder, P. Complete nucleotide sequence of the membrane form of the human IgM heavy chain. Nucleic Acids Res. (1990)18: 4278). If the aptamer binds only to the mIgM, these additional extracellular amino acids were postulated to play a significant role in defining the epitope specificity. Interestingly, a trypsin cleavage site is present at amino acid 430, at the border of the sequence difference between soluble and membrane bound mIgM (Rogers et al., 1980, op. cit.) Thus, the membrane-associated sequences proximal to amino acid 430 are present only in the membrane-bound form. Trypsinization to cleave off the domains of the membrane bound mIgM distal to this site, left only the most proximal region present on the cell membrane. At high concentrations of trypsin, there is a dramatic reduction in binding of goat anti-IgM antibody with Ramos cells but, TD05.1 does not change its binding significantly (FIG. 4). These data indicate that TD05.1 predominately interacts with the unique extra amino acid sequences of mIgM and not with the distal portions of IgM that are present in soluble, circulating IgM. CD20 is a non-glycolysated phosphoprotein expressed on early and mature normal B-cells at developmental stages that are the source of a variety of B cell neoplasms, including B-cell NHL and CLL (Meerten T V, Hagenbeek A. CD20-targeted therapy: The next generation of antibodies. Semi. in Hematology. (2010) 47: 199-210). Therefore, CD20 was used as a positive control for the enzymatic cleaving experiment.

FIG. 4 shows binding of TD05.1 to mIgM after trypsin treatment. Cells were treated with trypsin for 40 min and binding of FITC labeled (A) TD05.1, (B) anti-CD20, and (C) anti-IgM antibody, was evaluated and compared with untreated control.

We further investigated whether the epitope of the aptamer was restricted to the surface mIgM by measuring the binding of TD05.1 in the presence of soluble IgM. The aptamers were incubated with Ramos cells in the presence of a large excess of purified soluble IgM in binding buffer or in the presence of 20% human serum (containing approximately 90-300 mg/L IgM). An antibody specific for IgM heavy chain showed a dramatic reduction in binding to the cell membrane when free soluble pentameric IgM was present in the reaction (FIG. 5A). The aptamer binding was unaffected (FIG. 5B) showing that the epitope of the aptamer was restricted to cell membrane bound IgM. This specificity is critical to the feasibility of using this aptamer as a targeting vehicle in vivo. In addition to the monovalent aptamer, TetVA.8S was also assayed for its ability to specifically recognize the membrane bound heavy chain of the IgM when excess amount of soluble IgM (50%) was present in the binding buffer. The TetVA.8S binding to Ramos cells was unaffected when excess soluble IgM present; however, a decrease in binding was observed in 50% human serum (FIG. 5C). This decrease might be due to non-specific interactions with serum proteins other than soluble IgM which would decrease the effective concentration of the TetVA.8S.

Figure 5:
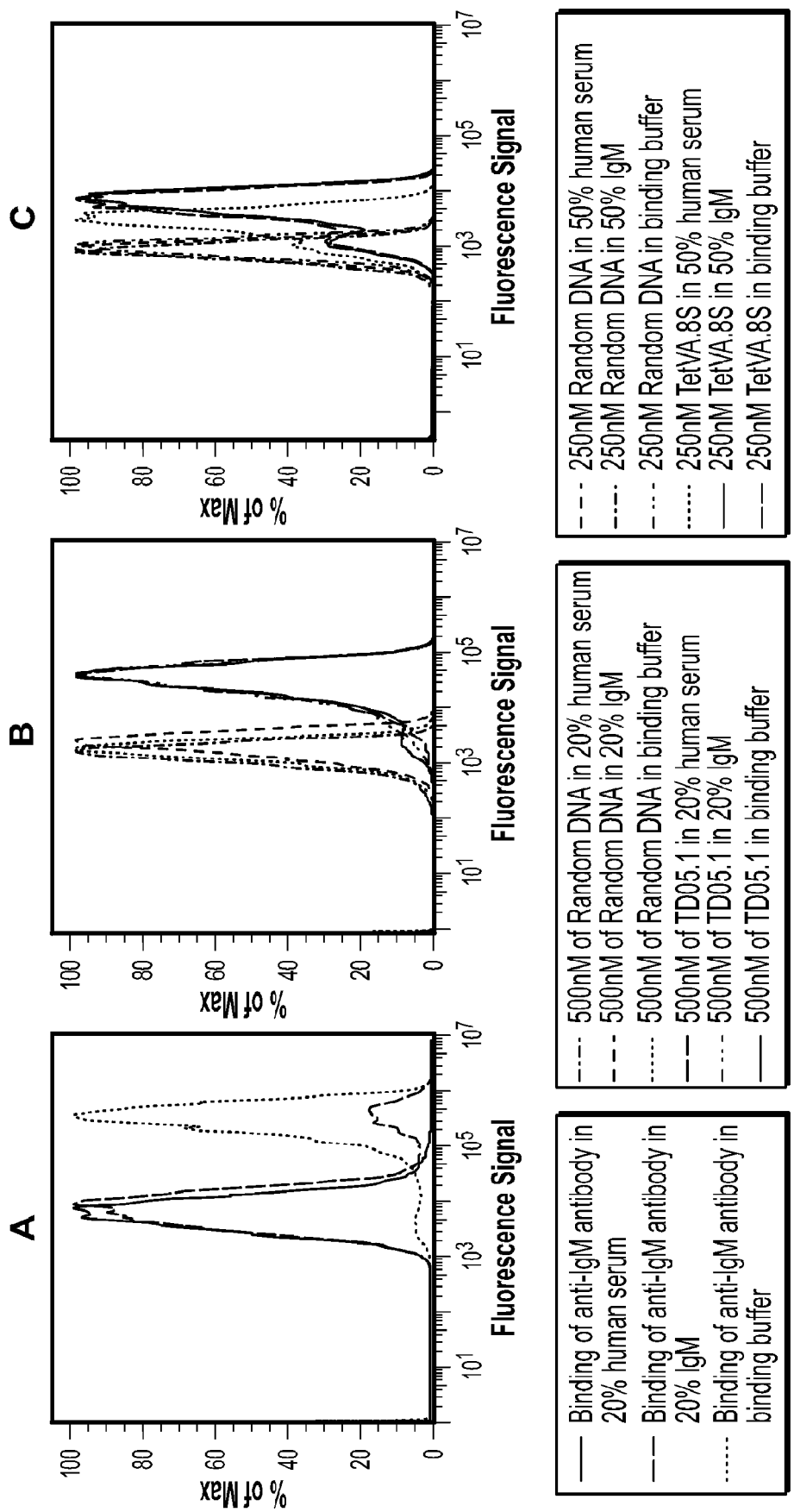
FIG. 5 shows the binding of aptamer in the presence of soluble IgM or human serum. The FITC labeled monomeric and tetrameric aptamer was incubated with Ramos cells in the presence of soluble IgM/human serum for 30 min, and subsequently washed and binding was analyzed using flow cytometry. (A) Positive control showing blocking of anti-IgM by serum or soluble IgM. (B) Monomeric aptamer binding is not affected when serum or excess soluble IgM is present. (C) Tetrameric aptamer binding is not significantly affected when serum and excess soluble IgM is present.

FIG. 5 shows binding of aptamer in the presence of soluble IgM or human serum. The FITC labeled Monomeric and tetrameric aptamer was incubated with Ramos cells in the presence of soluble IgM/human serum for 30 min, and subsequently washed and binding was analyzed using flow cytometry. (A) Positive control showing blocking of anti-IgM by serum or soluble IgM. (B) Monomeric aptamer binding is not affected when serum or excess soluble IgM is present. (C) Tetrameric aptamer binding is not significantly affected when serum and excess soluble IgM is present.

The trypsin cleavage experiments and cross-blocking with anti-IgM are most consistent with the aptamer binding epitope localizing to a segment of the mIgM unique to the proximal membrane portion of the molecule. However, these data could also be explained by conformational changes in the soluble IgM that hide the epitope at its proximal terminus. It is also possible that accessory molecules in the vicinity of the epitope on the cell surface allow for binding of the aptamer.

Figure 6:
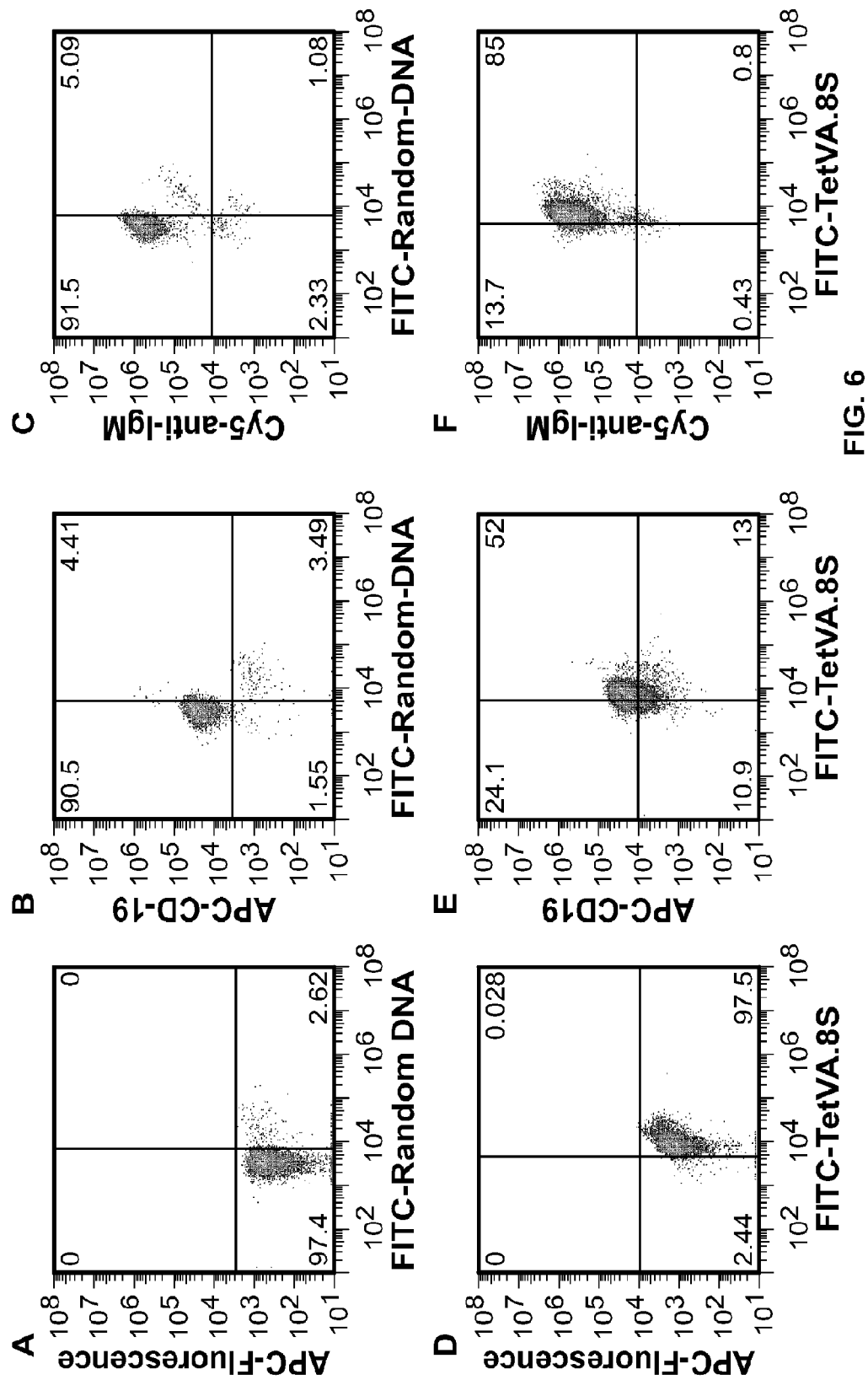
FIG. 6 shows the binding of TetVA.8S with Ramos cells in the intraperitoneal cavity of mice. 0.5 nmoles of either TetVA.8S or Random DNA in saline was injected into intraperitoneal cavity. Ramos cells were withdrawn from the intraperitoneal cavity and co-stained with control (BSA alone), cy5-labeled anti-IgM antibody or APC labeled anti-CD19. A: FITC-random sequence injected i.p.; (ex vivo BSA control), B: FITC-random sequence injected i.p.; co-stained with anti-CD19, C: FITC-random injected i.p.; co-stained with anti-IgM, D: FITC-TetVA.8S injected i.p.; (ex vivo BSA control), E: FITC-TetVA.8S injected i.p.; co-stained with anti-CD19, F: FITC-TetVA.8S injected i.p.; co-stained with cy-5-anti-IgM.

In Vivo Binding of TetVA.8S with Ramos Cells. The TetVA.8S was administered i.p. into mice bearing Ramos cells in their intraperitoneal cavities to investigate binding in vivo. TetVA.8S selectively recognized Ramos cells in the intraperitoneal cavity of live mice suggesting the feasibility of using this aptamer as a therapeutic carrier or agent (compare FIG. 6A vs 6D). Flow cytometry confirmed the specificity of the TetVA.8S binding to mIgM expressing B cells in vivo using excess anti-IgM antibody and anti-CD19 antibody as controls (FIG. 6 B, C,E,F). This experiment demonstrates at physiological conditions in a live mouse that the multivalent construct of the aptamer TD05 specifically recognizes its target epitope on Ramos cells.

FIG. 6 shows that binding of TetVA.8S with Ramos cells in the intraperitoneal cavity. 0.5 nmoles of either TetVA.8S or Random DNA in saline was injected into intraperitoneal cavity. Ramos cells were withdrawn from the intraperitoneal cavity and co-stained with control (BSA alone), cy5-labeled anti-IgM antibody or APC labeled anti-CD19. A: FITC-random sequence injected i.p.; (ex vivo BSA control), B: FITC-random sequence injected i.p.; co-stained with anti-CD19, C: FITC-random injected i.p.; co-stained with anti-IgM, D: FITC-TetVA.8S injected i.p.; (ex vivo BSA control), E: FITC-TetVA.8S injected i.p.; co-stained with anti-CD19, F: FITC-TetVA.8S injected i.p.; co-stained with cy-5-anti-IgM.

What is claimed is:

1. A multivalent aptamer having the sequence represented by SEQ ID NO:16, SEQ ID NO:15, SEQ ID NO:19 or SEQ ID NO:20.

2. A compound comprising the multivalent aptamer represented by SEQ ID NO:16, SEQ ID NO:15, SEQ ID NO:19 or SEQ ID NO:20.

3. An aptamer of claim 1 further comprising a therapeutic or diagnostic moiety.

4. A compound of claim 2 further comprising a therapeutic or diagnostic moiety.

5. The aptamer of claim 3 wherein the further moiety is a cytotoxic agent, a radionuclide, a fluorophore, an antibody, or a siRNA.

6. The compound of claim 4 wherein the further moiety is a cytotoxic agent, a radionuclide, a fluorophore, an antibody, or a siRNA.

7. A pharmaceutical composition comprising an aptamer of any one of claim 1, 3 or 5, or a compound of any one of claims 2, 4 or 6, and a pharmaceutically acceptable carrier, diluent or excipient.

8. A method for treating or diagnosing a B cell disease comprising administering to a subject in need thereof the pharmaceutical composition of claim 7.

9. The method of claim 8 wherein the B cell disease is cancer.

10. The method of claim 8 wherein the B cell disease is an autoimmune disease, an immune deficiency disease, a disease benefitted by immunosuppression or as an adjunct to vaccination or tolerization.

11. A method for treating or diagnosing a B cell disease comprising administering to a subject in need thereof the pharmaceutical composition of claim 7.

12. The method of claim 11 wherein the B cell disease is cancer.

13. The method of claim 11 wherein the B cell disease is an autoimmune disease, an immune deficiency disease, a disease benefitted by immunosuppression or as an adjunct to vaccination or tolerization.

14. A method for treating a cancer comprising administering to a subject in need thereof the pharmaceutical composition of claim 7.

15. The method of claim 14 wherein the cancer is Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, or mantle cell lymphoma.

16. A method for treating an autoimmune disease comprising administering to a subject in need thereof a pharmaceutical composition of claim 7.

17. The method of claim 16 wherein the autoimmune disease is lupus erythematosus, type I diabetes, rheumatoid arthritis, psoriasis, alopecia areata or anterior uveitis.

* * * * *